(12) United States Patent
Parkinson

(10) Patent No.: US 9,085,793 B2
(45) Date of Patent: Jul. 21, 2015

(54) EX VIVO METHODS TO IDENTIFY CIRCULATING DRUG METABOLITES WITH DRUG INTERACTION POTENTIAL

(71) Applicant: XPD Consulting, LLC, Shawnee, KS (US)

(72) Inventor: Andrew Parkinson, Shawnee, KS (US)

(73) Assignee: XPD CONSULTING, LLC, Shawnee, KS (US)

( * ) Notice: Subject to any disclaimer, the term of this patent is extended or adjusted under 35 U.S.C. 154(b) by 0 days.

(21) Appl. No.: 13/915,392

(22) Filed: Jun. 11, 2013

(65) Prior Publication Data

US 2013/0330737 A1  Dec. 12, 2013

Related U.S. Application Data

(60) Provisional application No. 61/658,222, filed on Jun. 11, 2012.

(51) Int. Cl.
| | | |
|---|---|---|
| C12Q 1/68 | (2006.01) | |
| G01N 33/68 | (2006.01) | |
| C12Q 1/26 | (2006.01) | |
| C12N 9/02 | (2006.01) | |

(52) U.S. Cl.
CPC .............. *C12Q 1/26* (2013.01); *G01N 33/6872* (2013.01)

(58) Field of Classification Search
None
See application file for complete search history.

(56) References Cited

U.S. PATENT DOCUMENTS

| | | | |
|---|---|---|---|
| 7,169,576 B2 | 1/2007 | Gan et al. | |
| 2008/0194421 A1 | 8/2008 | Borisy et al. | |
| 2010/0247683 A1 | 9/2010 | Roy et al. | |

FOREIGN PATENT DOCUMENTS

JP           2010165230 A           7/2010

OTHER PUBLICATIONS

Jeong et al., "Inhibition of drug metabolizing cytochrom P450s by the aromatase inhibitor drug letrozole and its major oxidative metabolite 4,4'-methanol-bisbenzonitrile in vitro" 64 Cancer Chemotherapy and Pharmacology 867-875 (2009).*
International Search Report and Written Opinion in corresponding PCT/US2013/045228 mailed Feb. 17, 2014.
Bjornsson TD, Callaghan JT, Einolf HJ, Fischer V, Gan L, Grimm S, Kao J, King SP, Miwa G, Ni L, Kumar G, McLeod J, Obach RS, Roberts S, Roe A, Shah A, Snikeris F, Sullivan JT, Tweedie D, Vega JM, Walsh J, Wrighton SA. The conduct of in vitro and in vivo drug-drug interaction studies: A Pharmaceutical Research and Manufacturers of America (PhRMA) perspective. Drug Metab Dispos31:815-832, 2003 (18 pages).
Chu V, Einolf HJ, Evers R, Kumar G, Moore D, Ripp S, Silva J, Sinha V, Sinz M and Skerjanec A. In Vitro and in Vivo Induction of Cytochrome P450: A Survey of the Current Practices and Recommendations: A Pharmaceutical Research and Manufacturers of America Perspective. Drug Metab Dispos37: 1339-1354, 2009 (16 pages).
EMA (2010). European Medicines Agency: Guideline on the investigation of drug interactions. http://www.ema.europa.eu/ema/pages/includes/document/open_document.jsp?webContentId=WC500090112 (38 pages).
EMA (1997). European Medicines Agency: Note for guidance on the investigation of drug interactions http://www.ema.europa.eu/docs/en_GB/document_library/Scientific_guideline/2009/09/WC500002966.pdf (14 pages).
FDA (2012). US Food and Drug Administration: Guidance for Industry. Drug interaction studies—Study design, data analysis, implications for dosing, and labeling recommendations. http://www.fda.gov/downloads/Drugs/GuidanceComplianceRegulatoryInformation/Guidances/UCM292362.pdf (79 pages).
FDA (2006). US Food and Drug Administration: Guidance for Industry: Drug Interaction Studies—Study Design, Data Analysis, and Implications for Dosing and Labeling. Draft Guidance. http://www.fda.gov/OHRMS/DOCKETS/98fr/06d-0344-gdl0001.pdf (55 pages).
Grimm SW, Einolf HJ, Hall SD, He K, Lim H-K, Ling K-HJ, Lu C, Nomeir AA, Seibert E, Skordos KW, Tonn GR, Van Horn R, Wang RW, Wong YN, Yang TJ and Obach RS. The Conduct of in Vitro Studies to Address Time-Dependent Inhibition of Drug-Metabolizing Enzymes: A Perspective of the Pharmaceutical Research and Manufacturers of America. Drug Metab Dispos 37:1355-1370; 2009 (16 pages).
Huang SM, Strong JM, Zhang L, Reynolds KS, Nallani S, Temple R, Abraham S, Habet SA, Baweja RK, Burckart GJ, Chung S, Colangelo P, Frucht D, Green MD, Hepp P, Karnaukhova E, Ko HS, Lee JI, Marroum PJ, Norden JM, Qiu W, Rahman A, Sobel S, Stifano T, Thummel K, Wei XX, Yasuda S, Zheng JH, Zhao H and Lesko LJ. New era in drug interaction evaluation: US Food and Drug Administration update on CYP enzymes, transporters, and the guidance process. J Clin Pharmacol 48:662-670, 2008 (9 pages).
Isoherranen N, Hachad H, Yeung CK and Levy RH. Qualitative analysis of the role of metabolites in inhibitory drug-drug interactions: Literature evaluation based on the metabolism and transport drug interaction database. Chem Res Toxicol 22: 294-298,2009 (5 pages).

(Continued)

*Primary Examiner* — Celine Qian
*Assistant Examiner* — Nancy J Leith
(74) *Attorney, Agent, or Firm* — Hovey Williams LLP

(57) ABSTRACT

Ex vivo methods of detecting and analyzing circulating drug metabolites with drug interaction potential are provided. The methods include the use of clinical plasma samples from subjects who have been administered an investigational drug in vivo. The clinical plasma samples will contain both the parent drug and associated metabolites. A control plasma sample spiked directly with the drug of interest can be used as a standard reference. The plasma samples can be applied to an in vitro test system to evaluate the changes in activity or expression of drug-metabolizing enzymes and/or drug transporters in the test systems to determine circulating drug metabolites with drug interaction potential. By comparing the clinical plasma sample to the drug-spiked control, the inhibitory and/or inducing effects on drug-metabolizing enzymes and/or drug transporters can be correctly attributed to the parent drug or its associated metabolites.

16 Claims, 11 Drawing Sheets
(3 of 11 Drawing Sheet(s) Filed in Color)

(56) References Cited

OTHER PUBLICATIONS

Kazmi F, Buckley DB, Yerino P, Ogilvie BW and Parkinson A. Effects of plasma on cytochrome P450 (CYP) inhibition studies in human liver microsomes (HLM): Consequences on in vitro to in vivo extrapolations (IVIVE). Poster 192 at the annual meeting of the International Society for the Study of Xenobiotics (ISSX) in Baltimore, Maryland, USA 2009 (1 page).

Lu C, Miwa GT, Prakash SR, Gan L-S and Balani SK. A novel model for the prediction of drug-drug interactions in humans based on in vitro cytochrome P450 phenotypic data. Drug Metab Dispos 35: 79-85, 2007 (7 pages).

Lu C, Hatsis P, Berg C, Lee FW and Balani SK. Prediction of pharmacokinetic drug-drug interactions using human hepatocyte suspension in plasma and cytochrome P450 phenotypic data. II. In vitro-in vivo correlation with ketoconazole. Drug Metab Dispos 36: 1255-1260, 2008a (6 pages).

Lu C, Berg C, Prakash SR, Lee FW and Balini SK. Prediction of pharmacokinetic drug-drug interactions using human hepatocyte suspension in plasma and cytochrome P450 phenotypic data. III. In vitro-in vivo correlation with fluconazole. Drug Metab Dispos 36: 1261-1266, 2008b (6 pages).

Mao J, Mohutsky MA, Harrelson JP, Wrighton SA and Hall SD. Prediction of CYP3A-mediated drug-drug interactions using human hepatocytes suspended in human plasma. Drug Metab Dispos 39: 591-602, 2011 (12 pages).

Mao J, Mohutsky MA, Harrelson JP, Wrighton SA and Hall SD. Predictions of cytochrome P450-mediated drug-drug Interactions using cryopreserved human hepatocytes: Comparison of plasma and protein-free media incubation conditions. Drug Metab Dispos 40: 706-716, 2012 (11 pages).

Obach RS, Walsky RL, Venkatakrishnan K, Houston JB, Tremaine LM. In vitro cytochrome P450 inhibition data and the prediction of drug-drug interactions: Qualitative relationships, quantitative predictions, and the rank-order approach. Clin Pharmacol Ther 78:582-592, 2005 (18 pages).

Obach RS, Walsky RL, Venkatakrishnan K, Gaman EA, Houston JB, Tremaine LM. The utility of in vitro cytochrome P450 inhibition data in the prediction of drug-drug interactions. J Pharmacol Exp Ther 316:336-348, 2006 (13 pages).

Ogilvie BW, Zhang D, Li W, Rodrigues AD, Gipson AE, Holsapple J, Toren P and Parkinson A. Glucuronidation converts gemfibrozil to a potent, metabolism-dependent inhibitor of CYP2C8: implications for drug-drug interactions. Drug Metab Dispos 34: 191-197, 2006 (7 pages).

Ogilvie BW, Usuki E, Yerino P and Parkinson A. In vitro approaches for studying the inhibition of drug-metabolizing enzymes and identifying the drug-metabolizing enzymes responsible for the metabolism of drugs (reaction phenotyping) with special emphasis on cytochrome P450. In: Drug-drug Interactions (Drugs and the Pharmaceutical Sciences)—Second edition (Ed.: A.D. Rodrigues). Informa Healthcare, pp. 231-358, 2008 (129 pages).

Parkinson A, Kazmi F, Buckley DB, Yerino P, Ogilvie BW, and Paris BL: System-dependent outcomes during the evaluation of drug candidates as inhibitors of cytochrome P450 (CYP) and uridine diphosphate glucuronosyltransferase (UGT) enzymes: human hepatocytes versus liver microsomes versus recombinant enzymes. Drug Metab Pharmacokinet 25:16-27, 2010 (12 pages).

Parkinson A, Kazmi F, Buckley DB, Yerino P, Paris BL, Holsapple J, Toren P, Otradovec SM, and Ogilvie BW: An evaluation of the dilution method for identifying metabolism-dependent inhibitors of cytochrome P450 enzymes. Drug Metab Dispos 39:1370-1387, 2011 (18 pages).

Shitara Y, Hirano M, Sato H and Sugiyama Y. Gemfibrozil and its glucuronide inhibit the organic anion transporting polypeptide 2 (OATP2/OATP1B1:SLC21A6)-mediated hepatic uptake and CYP2C8-mediated metabolism of cerivastatin: analysis of the mechanism of the clinically relevant drug-drug interaction between cerivastatin and gemfibrozil. J Pharmacol Exp Ther 311: 228-236 (2004) (9 pages).

VandenBrink BM and Isoherranen N. The role of metabolites in predicting drug-drug interactions: Focus on irreversible P450 inhibition. Curr Opin Drug Discov Devel. 13: 66-77, 2010 (21 pages).

Yeung CK, Fujioka Y, Hachad, Levy RH and Isoherranen N. Are circulating metabolites important in drug-drug interactions?: Quantitative analysis of risk prediction and inhibitory potential. Clin Pharmacol Ther 89: 105-113, 2011 (9 pages).

EMA (2012). European Medicines Agency: Guideline on the investigation of drug interactions. http://www.ema.europa.eu/docs/en_GB/document_library/Scientific_guideline/2012/07/WC500129606.pdf (60 pages).

* cited by examiner

Summary of process for evaluating the DDI potential of circulating metabolites

| Step 1 | Collect clinical plasma samples from subjects administered the drug under investigation. The clinical plasma could be used directly or diluted with control (pre-dose) plasma to generate a range of drug concentrations |
|---|---|
| Step 2 | Determine the concentration of parent drug in the clinical plasma samples |
| Step 3 | Add parent drug to control (pre-dose) plasma at concentrations that match or bracket those in the clinical plasma samples. These are the standard control plasma samples. They contain drug but not metabolites. |
| Step 4 | Add the clinical plasma sample(s), the standard control plasma samples and blank plasma (negative control) to the *in vitro* test system (cells or subcellular fractions). A positive control (blank plasma plus a known inhibitor or inducer) could be included at this stage. |
| Step 5 | Measure changes in the activity or expression of drug-metabolizing enzymes and drug transporters in the *in vitro* test system |
| Step 6 | Compare the inhibitory or inducing effects of the clinical plasma samples (which contains both parent drug and circulating metabolites) with those of the standard control plasma samples (which contain only parent drug). If the two samples are equipotent, inhibition or induction by the clinical plasma samples is ascribed to the parent drug. If the clinical plasma samples are more effective at inhibiting or inducing drug-metabolizing enzymes or drug transporters then the greater DDI potential is ascribed to circulating metabolites. |

Fig. 2

EX VIVO METHODS TO IDENTIFY CIRCULATING DRUG METABOLITES WITH DRUG INTERACTION POTENTIAL

CROSS-REFERENCE TO RELATED APPLICATIONS

The present application claims the priority benefit of U.S. Provisional Patent Application Ser. No. 61/658,222, filed Jun. 11, 2012, entitled AN EX VIVO METHOD TO IDENTIFY CIRCULATING DRUG METABOLITES WITH DRUG INTERACTION POTENTIAL, incorporated by reference in its entirety herein.

BACKGROUND OF THE INVENTION

1. Field of the Invention

The present invention relates to new methods of identifying, analyzing, and predicting drug interaction potential, and more specifically the ability of drug metabolites to alter the disposition of other drugs and thereby cause drug interactions.

2. Description of Related Art

Drugs have the potential to be the victim (object) or perpetrator (precipitant) of drug-drug interactions (DDIs), and for this reason, as part of the overall safety evaluation, regulatory agencies like the US Food & Drug Administration (FDA) and European Medicines Agency (EMA) require in vitro testing to ascertain which drug-metabolizing enzymes and drug transporters determine the disposition of a drug (to assess its victim potential) and which drug-metabolizing enzymes and drug transporters are inhibited or induced by a drug (to assess its perpetrator potential). To evaluate a drug's DDI perpetrator potential, the FDA and EMA require that all drugs (drug candidates or investigational drugs) be evaluated for their ability (1) to inhibit seven different cytochrome P450 (CYP) enzymes; (2) to induce three CYP enzymes, and (3) to inhibit 7 drug transporters, as shown in FIG. 1.

The FDA (2012) and EMA (2102) recently issued new guidelines on drug-drug interactions. Whereas previous versions of the guidelines (issued in 2006) focused on the ability of the parent drug to cause DDIs by inhibiting or inducing (i.e., by decreasing or increasing) the metabolism or transport of concomitantly administered drugs, the new guidelines focus on the DDI potential of both the parent drug and significant metabolites present in plasma (i.e., present in the circulation). Regulatory agencies define "significant circulating metabolite" in terms of systemic exposure to the metabolite relative to systemic exposure to the parent drug (both of which are measured as the area under the plasma concentration-time curve or AUC). The FDA defines a "significant circulating metabolite" as any metabolite with a plasma AUC≥25% of parent AUC; the EMA defines it as ≥25% of parent AUC and larger than 10% of the drug-related exposure. The number of significant circulating metabolites can be large. For example, if the parent drug accounts for only 10% of drug-derived material in plasma (based on plasma AUC) then, according the EMA's more restricted definition, there could be as many as nine significant circulating metabolites (each accounting for 10% of drug-related exposure, and each with a plasma AUC greater than 25% of parent drug AUC). There are numerous examples in the literature of drugs that cause clinically significant CYP inhibition due largely or partly to their conversion in vivo to inhibitory metabolites, as summarized in Table 1.

TABLE 1

Examples of drugs with circulating metabolites that contribute significantly to CYP inhibition in vivo

| | | | Parent Drug (P) | | | Metabolite (M) | | | |
|---|---|---|---|---|---|---|---|---|---|
| Parent (P) | Metabolite (M) | CYP | [I] (µM) | $K_i$ (µM) | [I]/$K_i$ | [I] (µM) | $K_i$ (µM) | [I]/$K_i$ | $IP_M/IP_P$ |
| Amiodarone | N-Desethylamiodarone | 2C9 | 2.5 | 94.6 | 0.026 | 1.5 | 2.3 | 0.67 | 25.3 |
| Bupropion | Threobupropion | 2D6 | 0.3 | 21 | 0.014 | 1.9 | 5.4 | 0.36 | 24.8 |
| | Hydroxybupropion | 2D6 | | | | 3.2 | 13 | 0.24 | 17.0 |
| | Erythrobupropion | 2D6 | | | | 0.37 | 1.7 | 0.22 | 15.3 |
| Sulfinpyrazone | Sulfinpyrazone sulfide | 2C9 | 17.8 | 229 | 0.031 | 5.0 | 27 | 0.19 | 6.0 |
| Venlafaxine | N-Desmethylvenlafaxine | 2D6 | 0.23 | 30 | 0.0078 | 0.93 | 20 | 0.047 | 6.0 |
| Atorvastatin | Atorvastatin lactone | 3A | 0.06 | 90 | 0.0007 | 0.003 | 0.9 | 0.004 | 5.5 |
| Amodiaquine | Desethylamodiaquine | 2D6 | 0.08 | 2.1 | 0.039 | 0.82 | 4.1 | 0.20 | 5.1 |
| Clomipramine | N-Desmethylclomipramine | 2D6 | 0.24 | 16 | 0.014 | 0.49 | 7.9 | 0.062 | 4.2 |
| Sertraline | N-Desmethylsertraline | 2D6 | 0.086 | 23 | 0.0038 | 0.14 | 16 | 0.009 | 2.4 |
| Risperidone | Paliperidone | 3A | 0.020 | 67 | 0.0003 | 0.046 | 80 | 0.001 | 2.0 |
| Sertraline | N-Desmethylsertraline | 3A4 | 0.33 | 3.5 | 0.094 | 0.53 | 3.5 | 0.15 | 1.6 |
| Haloperidol | Reduced haloperidol | 2D6 | 0.023 | 0.89 | 0.026 | 0.008 | 0.24 | 0.033 | 1.3 |
| Risperidone | Paliperidone | 2D6 | 0.020 | 6.9 | 0.0028 | 0.046 | 16 | 0.003 | 1.0 |
| Fluoxetine | Norfluoxetine | 2D6 | 0.37 | 0.2 | 2.2 | 0.38 | 0.2 | 2.0 | 0.92 |

Taken from a portion of Table 1 in a review article by Yeung et al., 2011, where CYP inhibition (Ki values) by the parent drug (P) and circulating metabolite(s) (M) were determined in vitro with synthetic standards.
[I] is the circulating plasma level (in vivo concentration) of inhibitor (parent drug or metabolite);
Ki is the inhibition constant determined in vitro;
$IP_M$ is the in vivo inhibitory potential of the metabolite(s), and
$IP_P$ is the in vivo inhibitory potential of the parent drug.

Bupropion, for example, has three circulating metabolites that are estimated to inhibit cytochrome P450 2D6 (CYP2D6) in vivo to a much greater extent (>10 fold) than bupropion itself (Table 1). Like the parent drug, significant circulating metabolites meeting the FDA and EMA criteria must be tested in vitro for their ability to function as perpetrators of DDIs (which can amount to a large number of metabolites if the parent drug is extensively metabolized to numerous metabolites). Accordingly, significant circulating metabolites must now be evaluated for their ability to (1) inhibit seven CYP enzymes; (2) induce three CYP enzymes, and (3) inhibit up to nine drug transporters (see FIG. 1). The focus on the DDI perpetrator potential of circulating metabolites in these new regulatory guidelines potentially translates into a considerable burden for pharmaceutical companies, which now face the prospect of having to identify, characterize, and synthesize each significant circulating metabolite and then conduct a large number of in vitro studies.

To comply with these new requirements, pharmaceutical companies can identify and synthesize each significant circulating metabolite and test each synthetic metabolite in vitro for its perpetrator potential, which is expensive and time-consuming, especially where a drug is converted to numerous metabolites. That is, under current methods, the assessment of the contribution of circulating metabolites to CYP inhibition in vivo is currently based on in vitro tests of CYP inhibition by both the parent drug and synthetic standards of its known circulating metabolite(s). This in vitro option was used to generate the data summarized in Table 1. In some cases, however, it is not possible to identify the structure or synthesize the metabolites of a drug (especially if the drug is a natural product with numerous chiral centers); hence, the in vitro approach to evaluating the DDI perpetrator potential of drug metabolites may not even be an option. Researchers can also conduct in vivo studies, which involve administering the drug under investigation together with so-called probe drugs whose disposition in vivo is known to reflect the activity of a particular drug-metabolizing enzyme or drug transporter. Such clinical DDI studies are usually conducted in healthy subjects but in some cases (such as when the drug under investigation is a toxic anti-cancer drug) they are conducted in patients. Such in vivo studies are considered superior to in vitro studies because the study subjects are exposed to the parent drug and its metabolites at pharmacologically relevant concentrations under clinical use conditions. However, to examine a drug's perpetrator potential for all seven of the CYP enzymes and all nine of the drug transporters listed in Table 1 would require a large number of clinical DDI studies, which would be expensive (perhaps prohibitively expensive) and time-consuming. In fact, based on published reports or package inserts (drug labels), no drug has undergone in vivo testing as a clinical inhibitor or inducer of all the CYP enzymes and drug transporters listed in Table 1.

Thus, there remains a need in the art for improved methods of identifying and predicting DDIs, particularly as they are attributable to metabolites of investigational drugs.

SUMMARY OF THE INVENTION

The present invention is broadly concerned with methods of analyzing drug metabolites with drug interaction potential. The methods comprise providing a clinical plasma sample from a subject administered the drug under investigation, wherein the clinical plasma sample comprises the administered drug at a first concentration and a plurality of metabolites of the drug. A standard control plasma sample is also provided, which comprises the drug (added to blank plasma in vitro) at a second concentration. The standard control plasma sample is essentially free of metabolites of the drug, but contains the drug at a concentration that is substantially the same as, or brackets, the first concentration. The clinical plasma sample is added to a first in vitro test system, and the standard control sample is added to a second in vitro test system. The changes in the activity or expression of drug-metabolizing enzymes and/or drug transporters in the first and second in vitro test systems is detected and analyzed to determine circulating drug metabolites with drug interaction potential, based upon these changes (which may indicate inhibitory and/or inducing effects on the drug-metabolizing enzymes and/or drug transporters).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 summarizes the inventive process flow for evaluating the DDI potential of drug metabolites;

DETAILED DESCRIPTION

Figure 1:
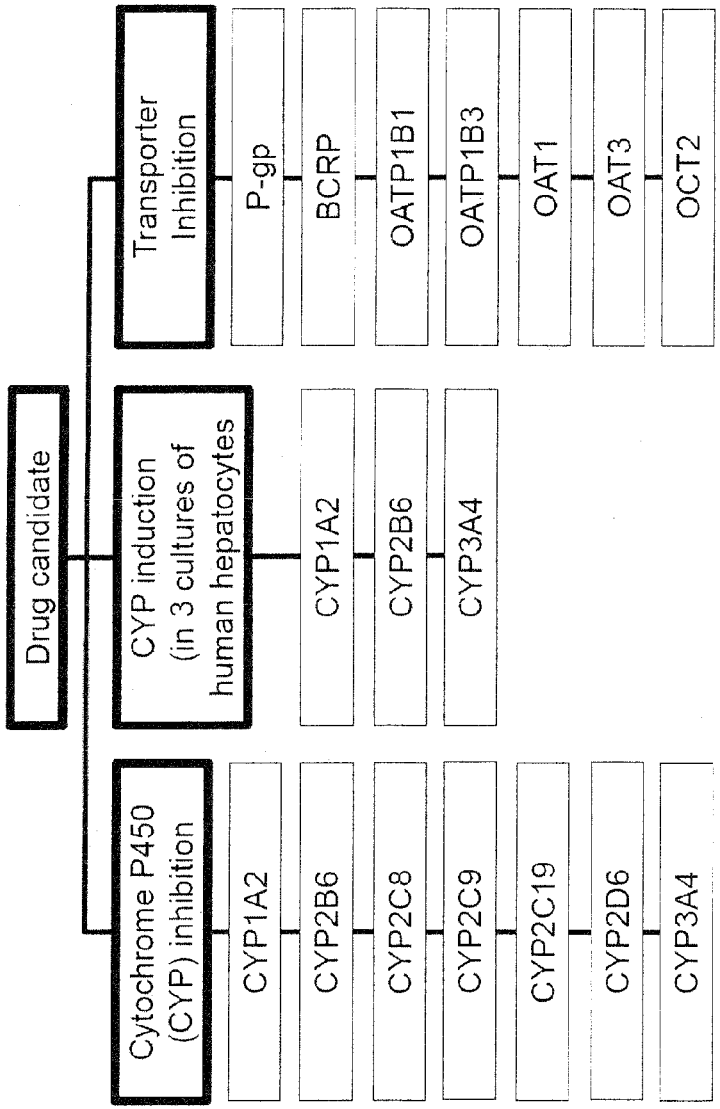
FIG. 1 lists the specific cytochrome P450 (CYP) enzymes and drug transporters whose inhibition or induction is a regulatory concern from a drug-drug interaction (DDI) perspective.

The present invention is concerned with ex vivo methods to identify the ability of circulating drug metabolites (metabolites of drugs in plasma or serum) to cause drug interactions by inhibiting or inducing cytochrome P450 (CYP), other drug-metabolizing enzymes, or drug transporters. As used herein, the term "metabolite" refers to compounds derived from the parent drug through metabolism or "spontaneous" chemical change. In other words, the parent drug is converted into its "metabolites" through in vivo metabolic pathways or non-enzymatic chemical processes. The term "circulating" metabolite, refers to metabolites circulating in blood. Typically, such circulating metabolites are of interest (from a safety perspective) when they are present in blood plasma at concentration levels and for sufficient time that systemic exposure to metabolites is equal to or greater than 10% (and for the purposes of DDIs, equal to or greater than 25%) of systemic exposure to the parent drug. However, the present method avoids the need to rely on an arbitrary threshold of 10% or 25% in assessing the DDI potential of circulating metabolites. The general process is illustrated in FIG. 2, and described in detail below.

Following oral administration of a drug, the drug is absorbed from the gastrointestinal tract such that plasma concentrations of the drug typically increase during the first several hours to reach a maximum (plasma Cmax) and then decline over time as the drug distributes into tissues and is metabolized (converted to metabolites, largely in the liver and, during absorption, the intestine) and eliminated (generally in bile and/or urine). The rate and timing of absorption, distribution, metabolism, and elimination (ADME) define the so-called pharmacokinetics of the drug in terms of Cmax (maximum plasma concentration), Tmax (time to reach Cmax), AUC (area under the plasma-concentration-versus-time curve) and half-life (the time to decrease the plasma concentration of drug by half during the elimination phase), which can differ widely from one drug to the next. The pharmacokinetics of a drug can change over time until steady state conditions are reached, which is determined by the plasma half-life. As a general rule, it takes five times the plasma half-life to reach steady state. For example, if the plasma half-life were 24 hours, it would take roughly five days to reach steady state. The same pharmacokinetic principle applies to circulating metabolites The EMA and FDA regulatory guidelines both recognize that the pharmacokinetics (including the half-lives) of circulating metabolites may differ from the pharmacokinetics of the parent drug (they may be shorter or longer). For this reason, both regulatory agencies recommend testing parent drug and significant circulating metabolites at plasma concentrations reached at steady state for both parent drug and metabolite(s) (at a time when there are no further time-dependent changes in the pharmacokinetics of the parent drug and metabolite[s]). It is at steady state that the highest concentrations of parent drug and metabolite(s) are present in plasma. According to the EMA and FDA, these "worse-case" concentrations should be considered in the design of in vitro studies to evaluate the potential of circulating metabolites to function as perpetrators of DDIs.

The value of the in vitro studies required by the FDA and EMA is that these relatively expensive studies can identify the relative risk of clinically significant DDIs. For example, in vitro studies can identify the rank order of potency of CYP inhibition by a drug. In other words, the CYP enzymes inhibited by the drug can be rank ordered from the most potently inhibited enzyme to the least potently inhibited enzyme. That is, when a drug is evaluated in vitro for its ability to inhibit more than one enzyme (such as the seven cytochrome P450 (CYP) enzymes listed in FIG. 1) it will inhibit some enzymes strongly and inhibit some enzymes weakly or not at all. The concentration of drug required to inhibit any given enzyme by 50% is called the $IC_{50}$ value (which stands for inhibitory concentration for 50% inhibition). The lower the $IC_{50}$ value, the more potently the drug inhibits the enzyme. The numerical values of $IC_{50}$ (or related measures of inhibitory potency, such as $K_i$) can be used to rank order the seven CYP enzymes from the most potently inhibited to the least potently inhibited. The in vitro rank order approach is highly, but not perfectly, predictive of clinical DDI potential; hence, the in vitro studies identify which enzyme or enzymes are of clinical concern with respect to drug interactions. For example, the enzyme of highest concern is the enzyme most potently inhibited by the investigational drug. If the in vivo administration of the investigational drug does not cause clinically significant inhibition of this enzyme (as determined in vivo with an appropriate probe drug) then it is unlikely to cause clinically significant inhibition of any of the less potently inhibited enzymes and no further clinical DDI studies are required. On the other hand, if this enzyme is inhibited in the clinic then a clinical study is performed to determine if the second most potently inhibited enzyme is also inhibited in vivo. In this way the in vitro rank order helps to prioritize clinical DDI studies and helps to identify a stopping point, which, depending on the outcome of the clinical DDI study, could be after testing the most potently inhibited enzyme, the second most potently inhibited enzyme, the third most potently inhibited enzyme and so forth.

The reason many in vitro tests are not perfectly predictive of in vivo DDI potential is that some drugs are converted in vivo to metabolites that contribute significantly to drug interactions, as shown in Table 1. This imperfection in the predictive power of in vitro tests of the parent drug is the rationale for the new regulatory guidelines on the need to consider significant circulating metabolites for their potential to cause drug interactions.

Although the role of circulating metabolites as perpetrators of drug interactions has only recently attracted the attention of regulatory agencies, the FDA and EMA have long recognized the role of metabolites in causing time-dependent inhibition (TDI) of cytochrome P450 (also known as metabolism-dependent inhibition or MDI). There are three primary mechanisms of TDI. The first two lead to irreversible or quasi-irreversible inhibition of a CYP enzyme. Irreversible inhibition involves the formation of a reactive metabolite that covalently modifies the cytochrome P450 apoprotein or destroys the heme moiety and thereby inactivates the enzyme. Quasi-irreversible inhibition involves the formation of a metabolite that forms a stable coordinate bond with the heme iron, which also causes prolonged inactivation of the enzyme. In both these cases, inhibition of cytochrome P450 can occur without release of the inhibitory metabolite from the enzyme's active site. Accordingly, the metabolites responsible for irreversible and quasi-irreversible CYP inhibition may not be "circulating" metabolites. The third mechanism of TDI involves the conversion of the drug to a metabolite that is a reversible inhibitor of cytochrome P450. In this case, the metabolite(s) released from the enzyme's active site can enter the systemic circulation. Examples of drugs falling into this third class of TDI (i.e., drugs that are converted to metabolites that are present in the circulation and can inhibit cytochrome P450) are listed in Table 1.

To aid in the identification of drugs that function as time-dependent inhibitors of cytochrome P450, the FDA and EMA recommend that in vitro studies of CYP inhibition be performed with and without a pre-incubation step. With a pre-incubation step (typically 30 min), the in vitro test system (typically human liver microsomes, recombinant human CYP enzymes or hepatocytes) is incubated with the investigational drug prior to the addition of the CYP marker substrate so that the investigational drug can be first converted to metabolites that might inhibit or inactivate one or more CYP enzymes in vitro. The new regulatory guidelines recognize that this pre-incubation step, while very informative for irreversible and quasi-irreversible inhibitors, can often underestimate the potential for the third type of TDI, the formation of metabolites that function as reversible inhibitor. This underestimation is a consequence of two phenomena. First, the inhibitory metabolite may be formed by an enzyme other than cytochrome P450, as is the case with bupropion and gemfibrozil. In other words, current in vitro tests can underestimate the range of inhibitory metabolites. Second, the inhibitory metabolite may accumulate in vivo to levels that rival or surpass those of the parent drug, as is the case with bupropion and fluoxetine (see Table 1). In vitro tests are rarely designed to allow such extensive accumulation of metabolites. In fact, according to the FDA (2006), in vitro tests should be performed so that the metabolism of the investigational drug (and marker substrates) is less than 30% and preferably less than 10%; hence, they can severely underestimate the extent to which metabolites can contribute to drug interactions. The potential for underestimating both the range and extent of inhibitory metabolites in conventional in vitro tests is the basis for the new regulatory guidelines on the importance of evaluating circulating metabolites for their potential to inhibit CYP enzymes and function as perpetrators of other drug interactions (namely enzyme induction and transporter inhibition).

Studies have been done previously in which plasma or serum was added to an in vitro test system to improve the predictive power of these tests. These studies were not performed with clinical plasma samples but were conducted with blank (drug-free) plasma/serum. Some of these studies were designed to evaluate the metabolic clearance of drugs (i.e., to measure the rate of disappearance of the parent drug) in rat or human hepatocytes in the presence and absence of plasma or serum. Other studies were designed to evaluate the inhibition of one or more CYP enzymes by one or more drugs in human hepatocytes or human liver microsomes in the presence and absence of plasma. In all of the studies, the purpose of adding plasma or serum was to approximate in vitro the same concentration of free (unbound) drug that is present in vivo. In all of these studies, the plasma or serum added to the in vitro test system was blank (control) plasma or serum (often from commercial sources). They were not clinical plasma/serum samples from subjects administered a drug in vivo. In fact, the human plasma/serum samples were purposefully from healthy, drug-free subjects to minimize the presence of potential interfering substances. Other previous studies have involved the addition of plasma samples to an in vitro test system (liver-derived cell lines) to examine their effect on hepatic function including CYP activity. However, the plasma samples were not from individuals administered a drug but were from patients with liver disease or sepsis; two diseases that impair liver function and drug metabolism in vivo. None of these studies were concerned with in vivo clinical plasma samples or evaluating the perpetrator potential of a drug and its metabolites.

In contrast, the inventive methods utilize clinical plasma samples to provide a more accurate ex vivo test system for identifying and predicting DDIs attributable to not just the parent drug itself, but also to its circulating metabolites.

In one or more embodiments, a biological sample from a subject (or subjects) who has been administered an investigational drug in vivo is provided. Thus, in one aspect, the method comprises first administering an investigational drug to a subject(s). The biological sample is then collected at various times from the subject, typically from about 1 to about 24 hours after the first administration of the drug and again after the drug has been administered repeatedly for about 7-10 days (or however long it takes to reach steady state). The biological sample could be collected numerous times over time from the same individual or at the same time from different individuals. It will be appreciated that the timing of collection can vary greatly depending on the study and the foregoing time frames are merely exemplary. The biological sample, as used herein, is plasma or serum which has been separated from whole blood. Thus, in some aspects, whole blood is collected from the subject, and then separated (e.g., by centrifugation) to collect the plasma or serum. Plasma is the soluble (cell free) fraction prepared from non-coagulated blood. It contains fibrinogen and other clotting factors. Serum is the soluble (cell free) fraction prepared from coagulated blood. It does not contain fibrinogen or other clotting factors. The term "plasma" is used herein interchangeably to refer to both "plasma" and "serum," unless otherwise specifically noted. The term "clinical plasma sample," is used herein to specifically refer to a sample (whether plasma or serum) obtained from a subject after administering an investigational drug to the subject in vivo, which sample then contains the investigational drug itself (also referred to as the "parent drug") and/or metabolites of the drug. The term excludes samples prepared by adding the drug to plasma in vitro or ex vivo, as well as samples from diseased individuals who have not been administered the drug of interest. Typically, the clinical plasma sample will contain the parent drug and all circulating metabolites at clinically relevant concentrations. Concentrations that range from Cmax (the maximum concentration) down to the limit of detection (the lowest detectable level) are considered to be "clinically relevant". The clinical plasma samples suitable for testing include individual or pooled plasma samples collected from a single-dose or multiple-dose clinical study (such those collected for pharmacokinetic analysis).

In one or more embodiments, the concentration of the parent drug in the clinical plasma sample(s) is measured to determine the reference concentration for the standard control sample (discussed below). The concentration of parent drug in the clinical plasma sample(s) is determined by any suitable analytical method. This is often accomplished by LC-MS (liquid chromatography with mass spectrophotometric detection), which is widely used to support pharmacokinetic studies, but any analytical method that can measure the parent drug could be used including liquid chromatography (HPLC or UPLC) with ultraviolet, visible, fluorescence, radiometric or other detection, gas-liquid chromatography (GLC), ELISA (enzyme-linked immunoassay) and other immunoassays. As noted above, the clinical plasma samples can be collected at various times from the same individual or at the same time from different individuals. In any case, the clinical plasma samples will likely contain a range of concentrations of parent drug. The clinical plasma sample(s) could be tested directly (i.e., as collected) or they could be diluted with blank (control) plasma to generate a range of concentrations of the parent drug (and any circulating metabolites) for analysis. For example, if the plasma sample was collected around Cmax at steady state, such that it contained relatively high levels of parent drug and any circulating metabolite(s), the sample could be diluted with blank plasma (such as pre-dose plasma) to permit determination of $IC_{50}$ or $EC_{50}$ (the concentration causing 50% inhibition or 50% of maximum induction).

A standard control sample is then prepared by providing a blank plasma sample (preferably a pre-dose plasma sample) to which the parent drug is directly added in vitro to the referenced concentration(s). For example, the appropriate level of the parent drug is added to the blank plasma at the same or substantially the same (i.e., within about 10%) concentrations as measured in the clinical plasma sample. Alternatively, multiple blank plasma samples could be "spiked" with a range of drug concentrations that "bracket" (e.g., from about one-tenth to about 10 times) the drug concentration in the clinical plasma sample. For example, at least two separate blank plasma samples can be provided, wherein the drug is added directly to one of the blank plasma samples at a first standard concentration that is less than the concentration of the drug in the clinical plasma sample, and also added to another of the blank plasma samples at a second standard concentration that is more than the concentration of the drug in said clinical plasma sample. In this way, the first and second standard concentrations "bracket" the concentration of the drug in the clinical plasma sample. In one or more embodiments, the first and second standard concentrations could respectively range from about 10 times less than the concentration of the drug in the clinical plasma sample to about 10 times more than the concentration of the drug in the clinical plasma sample. As another example, if the drug concentration in the clinical plasma sample was measured to be about 15 mg/L, then multiple standard control samples could be prepared with drug concentrations of about 1, 5, 10, 25, 50 and/or 100 mg/L. Thus, in the context of the present invention, this 100-fold range of drug concentrations is concerned to "bracket" the clinical drug concentration of 15 mg/mL. These plasma samples "spiked" in vitro with the parent drug, but no metabolites, serve as the standard controls. Blank (control) plasma samples (devoid of either the parent drug or its metabolites) can also be used to serve as negative controls. In other words, the standard control sample is essentially free of the drug's metabolites, while the blank control is essentially free of both the parent drug and the metabolites. As used here, the term "essentially free" means that the component is not intentionally or purposefully included in or added to the sample, although it is recognized that incidental or inconsequential (i.e., clinically insignificant) amounts may inadvertently or naturally be present in the sample. The blank (control) plasma used to prepare the standard controls and negative controls could be "pre-dose" plasma samples collected from the same individuals who participated in the clinical study (i.e., plasma samples collected from the individuals before administration of the investigational drug) or, if pre-dose plasma is not available, they could be pooled plasma samples from drug-free individuals (such plasma samples are commercially available). Blank plasma samples spiked in vitro with known inhibitors or inducers can also be used to serve as positive controls. The FDA (2006, 2012) and EMA (2006, 2012) provide lists of recommended or acceptable inhibitors/inducers that can be used in in vitro tests of CYP inhibition, CYP induction, and transporter inhibition. These positive controls are widely used by pharmaceutical companies, contract research organizations (CROs), and academia. Examples are listed in Table 2.

TABLE 2

Examples of inhibitors and inducers used as positive control in in vitro assays of CYP and transporter activity

| CYP enzyme | Direct inhibitor | TDI | Drug transporter | Positive control - inhibitors |
|---|---|---|---|---|
| Positive control - inhibitors | | | | |
| CYP1A2 | α-Naphthoflavone | Furafylline | P-gp | Valspodar (PSC833) or verapamil |
| CYP2B6 | Orphenadrine | Phencyclidine | BCRP | Ko143 or Ko134 |
| CYP2C8 | Montelukast | Gemfibrozil glucuronide | OATP1B1 | Rifampin |
| CYP2C9 | Sulfaphenazole | Tienilic Acid | OATP1B3 | Rifampin |
| CYP2C19 | Modafinil | S-Fluoxetine | OAT1 | Probenecid |
| CYP2D6 | Quinidine | Paroxetine | OAT3 | Probenecid |
| CYP3A4 | Ketoconazole | Troleandomycin | OCT2 | Quinidine |
| Positive controls - inducers | | | | |
| CYP1A2 | Omeprazole | | | |
| CYP2B6 | Phenobarbital | | | or CITCO |
| CYP3A4 | Rifampin | | | |

TDI: Time-dependent inhibitor (also known as metabolism-dependent inhibitor or MDI)

The clinical plasma samples are added to an in vitro test system to evaluate the impact of the parent drug and its circulating metabolites on drug-metabolizing enzymes and/or drug transporters. The standard control sample(s), negative control, and/or positive control (if present) are also added to respective in vitro test systems (which are the same type of system and assay used with the clinical plasma sample(s)). Suitable in vitro test systems include cultures of cells and/or subcellular fractions, which are assayed using an appropriate marker substrate(s), reporter(s), and/or probe(s) (depending on the test system used) to permit detection of the activity occurring in the system. For example, the in vitro test systems can include isolated hepatocytes (suspended or in culture), liver or intestinal microsomes, vesicles, other subcellular fractions, recombinant drug-metabolizing enzymes, recombinant transporters, purified drug-metabolizing enzymes, isolated cells expressing one or more drug-metabolizing enzymes and/or drug transporters, and/or cells lines expressing one or more drug-metabolizing enzymes and/or drug transporters. The in vitro systems typically used for in vitro testing of DDI potential are listed below in Table 3.

TABLE 3

In vitro systems used to evaluate the perpetrator potential of drugs and other chemicals

| DDI potential | In vitro test system |
| --- | --- |
| Inhibition of cytochrome P450 and other drug-metabolizing enzymes | Cellular systems<br>Hepatocytes (suspended or plated)<br>Cell lines or immortalized human hepatocytes (e.g., Hepa/RG)<br>Cells or microorganisms expressing one or more recombinant human drug-metabolizing enzyme<br>Subcellular fractions<br>Human liver/intestinal/kidney/lung microsomes, S9 fraction (post-mitochondrial supernatant), mitochondria or cytosol<br>Membranes containing one or more recombinant human drug-metabolizing enzyme |
| Induction of cytochrome P450 and other drug-metabolizing enzymes | Plated human hepatocytes (fresh or cyropreserved)<br>Cell lines or immortalized human hepatocytes (e.g., Hepa/RG, Fa2N-4 cells)<br>Reporter gene systems (cells transfected with a reporter gene under the control of a human xenosensor to detect drug-mediated activation of AhR, CAR, PXR and/or PPARα). |
| Inhibition of drug transporters | Cellular systems<br>Hepatocytes (suspended or plated) or immortalized human hepatocytes (e.g., Hepa/RG)<br>Cell lines (e.g., Caco-2 cells)<br>Cells expressing one or more recombinant human drug transporters (MDCK cells, HEK293 cells and others)<br>Subcellular fractions<br>Membrane vesicles usually prepared from cells expressing one or more recombinant human drug transporters |

These in vitro test systems are recognized by regulatory agencies and are widely used in pharmaceutical companies, CROs, and academia to investigate the DDI potential of drugs and other chemicals. Based upon previous studies using (blank) plasma, discussed above, the volume of sample added to the in vitro system can vary but the practical upper limit is around 96% (v/v) of the total incubation volume (e.g., 96 μL of a 100 μL incubation mixture); the remainder is the volume of the test system and assay itself, such as hepatocytes plus marker substrate or human liver microsomes plus cofactor (NADPH) plus marker substrate. Assays for detection and analysis of enzyme/transporter activity within the system are commercially available and include any number of different types of probes, substrates (e.g., fluorogenic), reporters, and the like. Some exemplary assay systems include human liver microsomes for CYP inhibition studies, cultured human hepatocytes for CYP induction studies, and human cell lines or cells transfected with human transporter genes (or membrane vesicles prepared from such cells) for transporter studies.

The activity or expression of drug-metabolizing enzymes or drug transporters in the in vitro test system is then monitored and detected. In the case of CYP inhibition (or inhibition of other drug-metabolizing enzymes) or transporter inhibition, the activity of the enzyme or transporter under investigation is typically measured with a marker substrate or ligand. In the case of CYP induction, the activity of the enzyme is usually measured with a marker substrate or the expression of the enzyme is measured based on changes in CYP mRNA levels. In one or more embodiments, the clinical plasma samples are also pre-incubated with the test system (prior to the addition of CYP marker substrate) to assess whether the parent drug and any circulating metabolites can function as time- or metabolism-dependent inhibitors (TDI/MDI). For example, the clinical plasma sample is added to the in vitro test system and pre-incubated, followed by adding enzyme and/or transporter marker substrates and/or ligands to the in vitro test system after pre-incubating. The system is then further incubated to detect changes in the activity or expression of the drug-metabolizing enzymes and/or drug transporters, and compared to results from parallel tests run with the standards, positive, and negative controls without pre-incubation. The FDA and EMA have recommended a variety of enzyme and transporter marker substrates suitable for use in the invention, and they are widely used by pharmaceutical companies, CROs and academia. Table 4 gives an example of a marker substrate for each of the CYP enzymes of specific interest to the FDA and EMA (namely CYP1A2, CYP2B6, CYP2C8, CYP2C9, CYP2C19, CYP2D6 and CYP3A4). Table 4 also gives examples of the substrates/ligands commonly used to assess the activity of the nine transporters of specific interest to the FDA and EMA (namely P-gp, BCRP, OATP1B1, OATP1B3, OAT1, OAT3 and OCT2).

TABLE 4

Examples of substrates/ligands used as in vitro probes of CYP activity and transporter function

| CYP enzyme | Marker substrate (and reaction) | Drug transporter | Marker substrate/ligand |
| --- | --- | --- | --- |
| CYP1A2 | Phenacetin (O-dealkylation) | P-gp | Digoxin |
| CYP2B6 | Efavirenz (8-hydroxylation) | BCRP | Prazosin |
| CYP2C8 | Amodiaquine (N-dealkylation) | OATP1B1 | Estradiol-17β-glucuronide |
| CYP2C9 | Diclofenac (4'-hydroxylation) | OATP1B3 | Estradiol-17β-glucuronide |
| CYP2C19 | S-Mephenytoin (4'-hydroxylation) | OAT1 | 4-Aminohippuric acid |
| CYP2D6 | Dextromethorphan (O-demethylation) | OAT3 | Estrone-3-sulfate |
| CYP3A4 | Midazolam (1'-hydroxylation) | OCT2 | Metformin |

However, it will be appreciated that any suitable technique for detecting and measuring enzyme or transporter activity can be used in the inventive methods. The concentration of CYP marker substrate added to the system is selected to be clinically relevant (e.g., Cmax) and, hence, below Km in the presence of plasma (and not equal to Km as is standard practice in buffer). In terms of the concentration of the biological component (hepatocytes, human liver microsomes or recombinant human proteins), incubation (and pre-incubation) times, stop reagents, internal standards and analysis of metabolites to measure CYP activity (or transporter activity), the assays performed in the presence of plasma are otherwise the same as those typically performed in buffer. Accordingly, the assays can advantageously be carried out following established standard operating procedures or manufacturer protocols for a given assay system, except for the deviations noted herein. Exemplary methods for detecting assay activity include measurements of the disappearance or translocation of the probe substrate or formation of one or more metabolites of the probe substrate by analytical procedures that include, but are not limited to, LC-MS, liquid chromatography (HPLC or UPLC) with ultraviolet, visible, fluorescence, radiometric or other detection, gas-liquid chromatography (GLC), ELISA (enzyme-linked immunoassay) and other immunoassays, or analysis of radioactivity when the probe substrate is radioactive.

Once the data are collected from the assay, the inhibitory or inducing effects of the clinical plasma samples (which contains both parent drug and circulating metabolites) with those of the standard controls (which contain only parent drug) can then be analyzed and compared. Advantageously, use of the standard curve sample allows the effects of the parent drug to be distinguished from that of its metabolite(s). For example, if the clinical plasma samples and the standard/control samples spiked with the same (reference) concentration of parent drug have the substantially the same DDI potential (for example, if they inhibit CYP enzymes to the same extent), then the DDI potential observed with the clinical plasma samples can be attributed to the parent drug (meaning there are no circulating metabolites at clinically relevant concentrations with significant DDI potential). In other words, if the two samples are equipotent, inhibition or induction by the clinical plasma samples is attributed to the parent drug. The results are considered to be "substantially the same" or "equipotent" if they agree to within some preset cutoff value (such as a 25% difference or a two-fold difference). Regulatory agencies do not prescribe such cutoff values. In the case of TDI/MDI experiments, for example, cutoff values are not specified in the FDA or EMA guidance documents leaving investigators to develop their own criteria (their own cutoff values) to assess whether or not metabolism of a drug increases its ability to inhibit CYP enzymes. Cutoff values for TDI/MDI (based on the magnitude of $IC_{50}$ shifts) range widely from one pharmaceutical company to the next (from as low as 1.2 to as high as 10 fold (Grimm et al., 2009)).

If the clinical plasma samples have substantially greater DDI potential than the standard controls (containing the same concentration of parent drug) (e.g., if the clinical plasma samples cause a greater degree of CYP inhibition than the standard control), then the additional DDI potential observed with the clinical samples can be attributed to one or more metabolite(s). In other words, if the clinical plasma samples are substantially more effective at inhibiting or inducing drug-metabolizing enzymes or drug transporters then the greater DDI potential is ascribed to circulating metabolites. The clinical plasma samples are considered to have "substantially greater DDI potential" or to be "substantially more effective" if the greater degree of inhibition exceeds 25% or a pre-determined cutoff value set by the investigator. A rank order approach can be applied to the results obtained with the clinical plasma samples to guide the need or prioritization of subsequent clinical DDI studies. The rank order approach refers to the process of ranking enzymes or transporters from the most potently or extensively inhibited enzyme/transporter to the least potently or extensively inhibited enzyme/transporter, as described herein. The presence of inhibitory metabolites in the clinical plasma sample may change the rank order of enzyme/transporter inhibition observed with the standard control sample (containing only the parent drug) and thereby identify a different enzyme/transporter as the most likely enzyme/transporter to be inhibited in the clinic. Thus, the inventive methods provide a more accurate prediction of DDI potential for an investigational drug, and also allow additional research into the compound to be more focused, increasing the efficiency and decreasing the costs associated with bringing new therapeutic compounds to patients.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these methods are provided by way of illustration and nothing therein should be taken as a limitation upon the overall scope of the invention.

Example 1

The following protocol describes the steps involved in comparing the ability of a clinical plasma sample (containing both drug and metabolites) with standard plasma samples (containing only drug) to inhibit the activity of the various CYP enzymes in human liver microsomes, but the protocol is applicable to other test systems (hepatocytes, cell lines, vesicles, recombinant or purified enzymes or other subcellular fractions) and other endpoints (inhibition of other drug-metabolizing enzymes and transporters and CYP induction).

1. Collect clinical plasma samples, determine the concentration of drug and prepare standard plasma samples:
   a. Prepare clinical plasma (or serum) from blood sample(s) collected before and after the administration of the drug under investigation.
   b. Determine the concentration of drug in the post-dose plasma sample(s) by LC-MS or another suitable analytical method.
   c. If the concentration of drug is high, dilute the clinical sample with blank (pre-dose) plasma (for example serially dilute the original sample two-fold, four-fold, eight-fold, etc.).
   d. Prepare standard plasma samples by adding the drug to the blank plasma samples. The concentration of drug added to the blank plasma samples should match or bracket that in the clinical plasma sample(s).
   e. Prepare positive controls by adding a known CYP inhibitor to blank plasma and negative controls (blank plasma or blank plasma containing the same amount of solvent used to add drug to the standard samples).
2. Prepare human liver microsomes (Reagent 1), the CYP marker substrate (Reagent 2) and the cofactor NADPH (Reagent 3), all of which are commercially available, as follows:
   a. Reagent 1: Thaw the frozen microsomal sample and, if necessary, dilute the sample in 0.25M sucrose to a protein concentration of 20 mg/mL.
   b. Reagent 2: Weigh out the CYP marker substrate (usually an approved drug) and dissolve it in a suitable solvent (water or an organic solvent such as methanol, acetonitrile or DMSO) to a concentration that is 500 times greater than the desired final concentration (one that is close to the clinically observed maximum concentration [Cmax] of the marker substrate in vivo). A different marker substrate is used for each CYP enzymes (see Table 5).
   c. Reagent 3: Weigh out NADPH or prepare an NADPH-generating system (both are commercially available) in phosphate or Tris buffer (50 mM, pH 7.4) to give a concentration of 33.3 mM NADPH.
3. Combine the reagents in a microtiter plate or similar apparatus and incubate at 37° C. to allow the CYP enzymes in human liver microsomes to metabolize the marker substrate in the presence of the various plasma samples. Prior to the incubation at 37° C. keep the microtiter plate and all reagents on ice (i.e., at about 4° C.).
   a. Dispense 90 µL of the clinical plasma samples (drug+metabolites), the standard plasma samples (drug), and blank plasma (negative control) into separate wells of a 96-well microtiter plate.
   b. Add 5 µL of Reagent 1 (human liver microsomes) to each well. After all reagents are added the final concentration of human liver microsomes will be 0.1 mg/mL, but higher or lower protein concentrations can be used.
   c. Add 2 µL of Reagent 2 (the CYP marker substrate) to each well. The final concentration of marker substrate will clinically relevant (e.g., equal to Cmax) although higher and lower concentrations can be used.
   d. Add 3 µL of Reagent 3 (NADPH) to each well. The final concentration of NADPH will be 0.1 mM but higher and lower concentrations can be used.
   e. Incubate the microtiter plate at 37° C. in a water-bath or similar apparatus for a relatively short time (5-15 min) if CYP activity is to be measured based on the rate of formation of a metabolite from the marker substrate or for a relatively long time (15-60 min) if CYP activity is to be measured based on the rate of disappearance of the marker substrate.
4. Stop the reaction and analyze the samples.
   a. Stop the reactions by adding a stop reagent (usually an equal volume [100 µL] of organic solvent like methanol or acetonitrile) containing, if available, an internal standard (such as an isotopically labeled version of the substrate or metabolite to be analyzed) to assist in the subsequent analysis by LC-MS.
   b. Centrifuge the samples to remove precipitated protein.
   c. Transfer the supernatant fraction to a second microtiter plate or vials for analysis by LC-MS or another suitable analytical procedure.
5. Determine CYP activity based on the amount of substrate lost per minute or the amount of metabolite formed per minute and normalize rates to the amount of microsomal protein in the incubation mixture.
6. Compare CYP activity measured in the presence of (1) blank plasma containing no drug or metabolites, (2) the standard plasma sample containing only the drug, and (3) the clinical plasma sample (containing both drug and metabolites).
   a. Set the enzymatic rate determined in the presence of blank plasma to 100%.
   b. Express the enzymatic rates determined in the presence of the clinical and standard plasma samples as a percentage of the rate determined with the blank plasma sample. Values less than 100% indicate inhibition.
   c. Evaluate whether the degree of CYP inhibition caused by the clinical plasma samples is greater (by 25% or some other preset cutoff value) than that caused by the standard clinical samples.
   d. In the case of diluted plasma samples, determine $IC_{50}$ values and evaluate whether the $IC_{50}$ value determined with the clinical plasma samples is lower (by 1.5-fold or some other present cutoff value) than that determined with the standard plasma samples.

This procedure is for an evaluation of the ability of the drug and its metabolites in clinical plasma samples to cause direct inhibition of various CYP enzymes in human liver microsomes. To assess the potential for time-dependent inhibition (TDI), the samples (plasma+microsomes+cofactor) are incubated at 37° C. for 30-60 min prior to the addition of the marker substrate. After this preincubation period the marker substrate is added and the samples are incubated, treated with stop reagent, processed and analyzed as described above. The volume/concentration of reagents and the incubation volumes/times listed above are typical but considerable variation can be accommodated. For practical reasons it is difficult to increase the volume of plasma added to more than 96% of the total incubation volume. In the above example it was set to 90% for simplicity.

Example 2

Figure 3A:
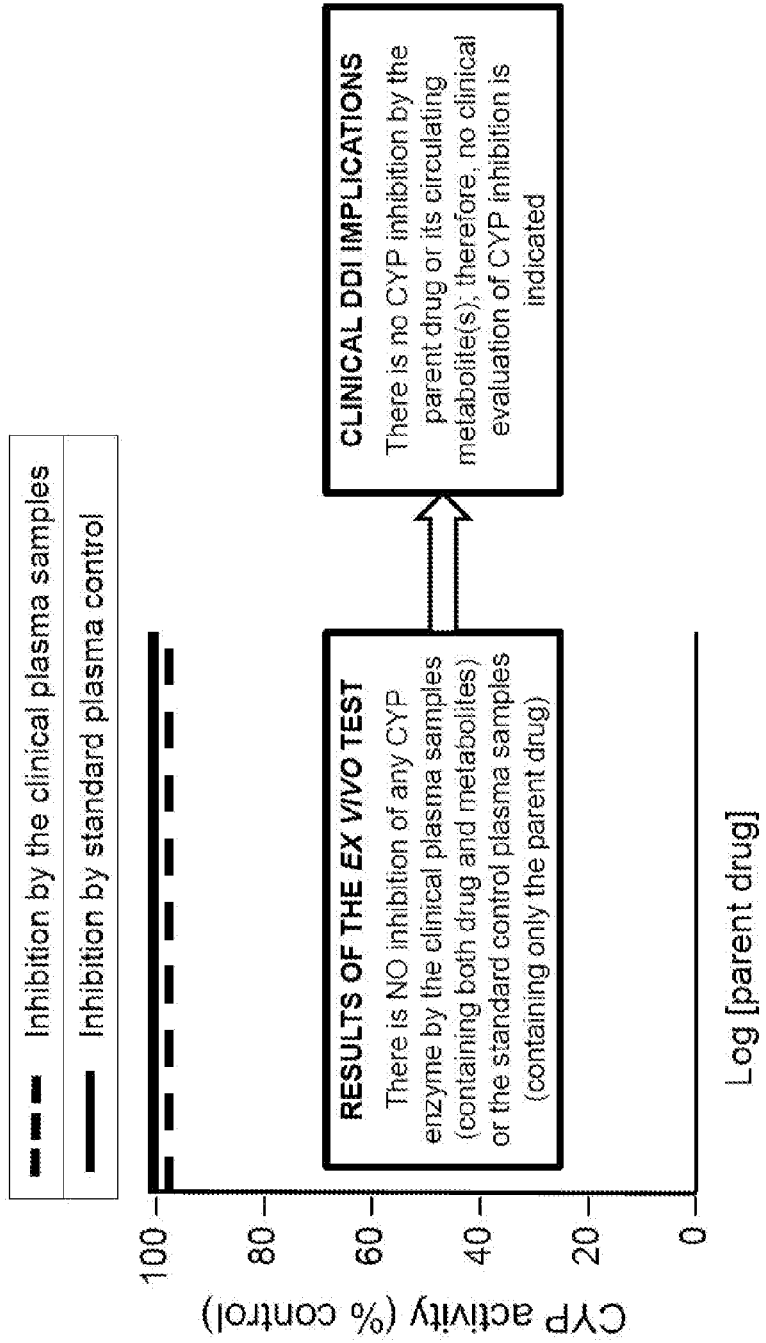
FIG. 3A shows simulated results of the ex vivo test described herein with no CYP inhibition by either the parent drug or metabolite(s).
Figure 3B:
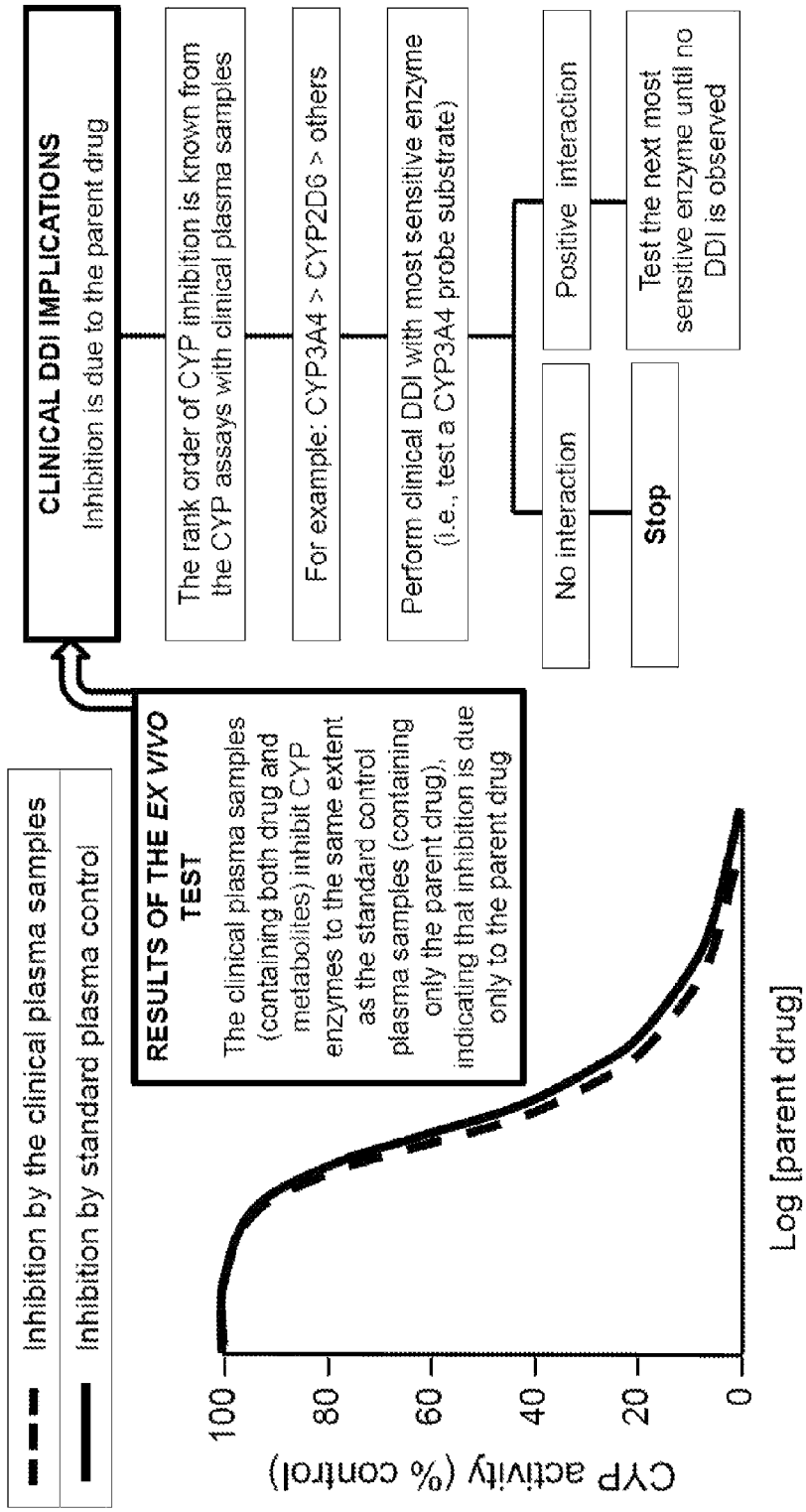
FIG. 3B shows simulated results of the ex vivo test described herein with inhibition by only the parent drug.
Figure 3C:
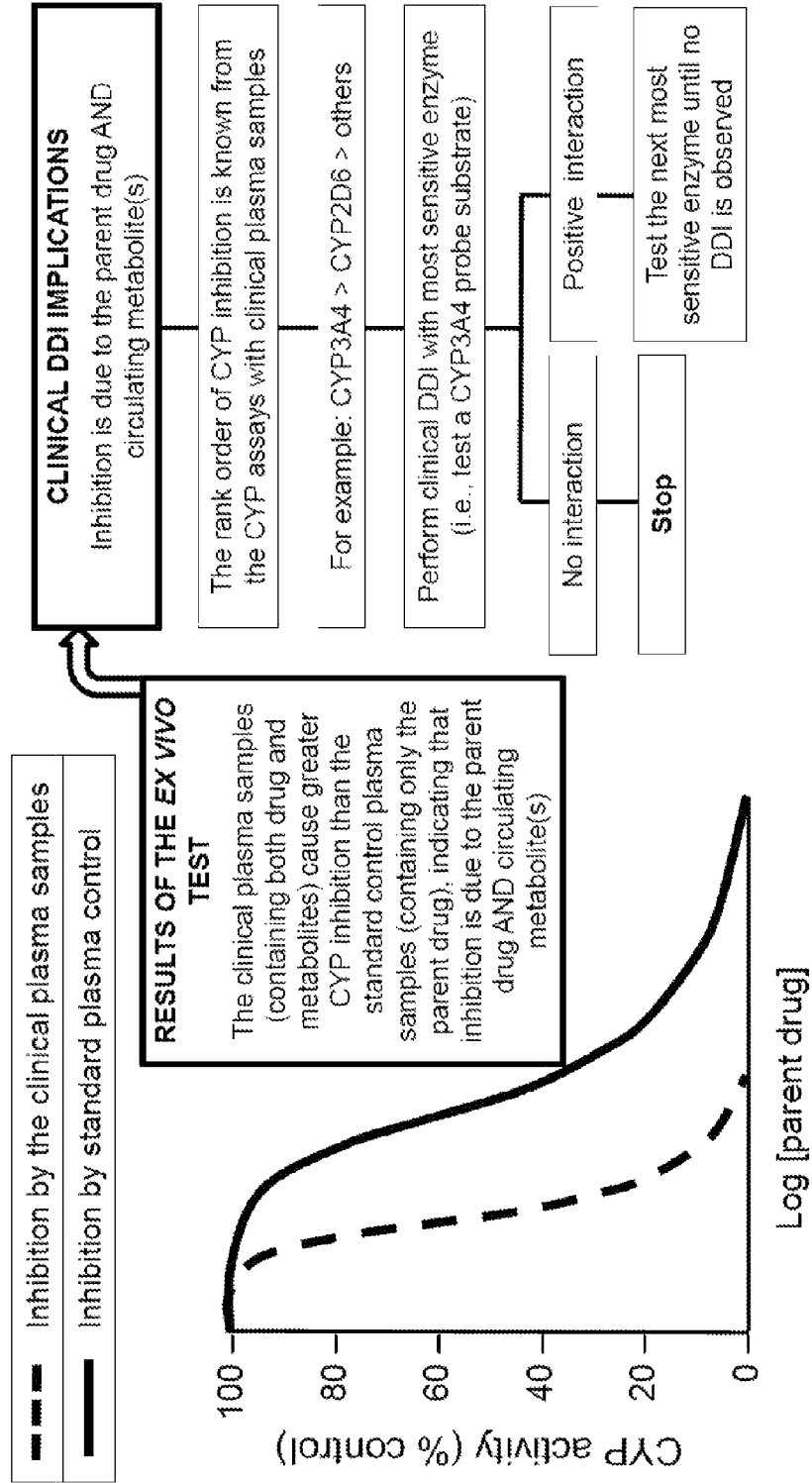
FIG. 3C shows simulated results of the ex vivo test described herein with the inhibition by both the parent drug and metabolite(s).
Figure 3D:
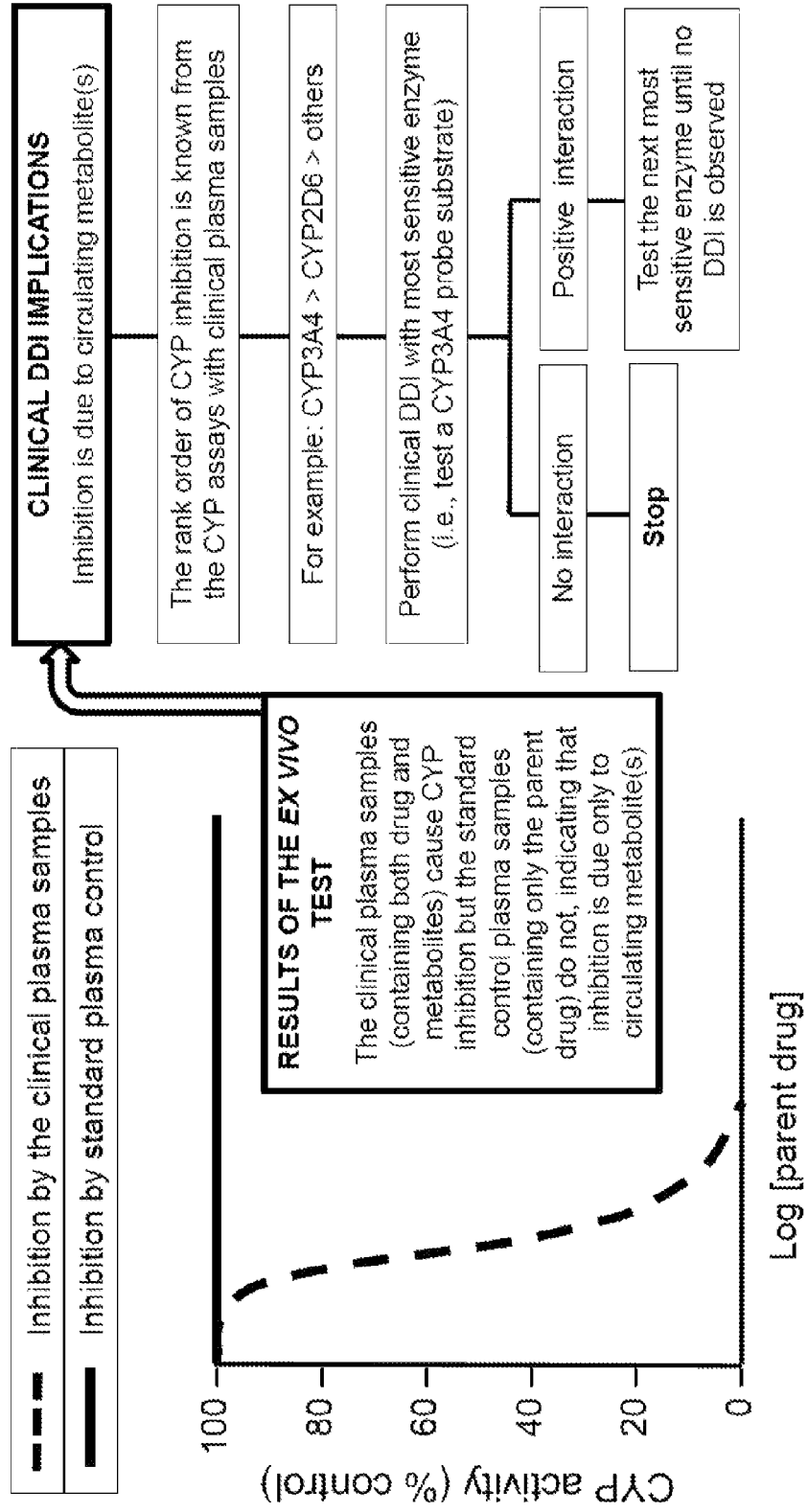
FIG. 3D shows simulated results of the ex vivo test described herein with inhibition by only the metabolite(s). These results guide the need or prioritization of clinical DDI tests based on the rank order approach (using CYP inhibition as an example).

Using CYP inhibition as an example, the addition of the in vivo clinical plasma samples to the in vitro test system (human hepatocytes, human liver microsomes or recombinant human enzymes), which is followed by a measurement of CYP activity, will produce four types of results, which are illustrated in FIG. 3A-3D:

1. No CYP inhibition (FIG. 3A);
2. CYP inhibition due only to the parent drug, as evidenced by the same degree of CYP inhibition by the clinical plasma samples as the control plasma samples spiked with the same concentration of parent drug (FIG. 3B);
3. CYP inhibition due to both the parent drug and circulating metabolite(s), as evidenced by CYP inhibition by the control plasma samples spiked with parent drug but an even greater degree of inhibition by the clinical plasma samples (FIG. 3C); or
4. CYP inhibition due only to the circulating metabolite(s), as evidenced by CYP inhibition by the clinical plasma samples despite a lack of inhibition by the control plasma samples spiked with the same concentrations of parent drug (FIG. 3D).

The inventive methods can also be used to evaluate the DDI perpetrator potential of clinical plasma samples from almost any type of clinical study that involves the in vivo administration of the investigational drug and the collection of blood samples (from which plasma or serum is obtained).

Although the invention can identify the presence of circulating metabolites with DDI potential, it does not establish the identity of the inhibitory/inducing metabolites. However, the information obtained from the inventive methods is still enormously valuable and useful. That is, regardless of whether the clinical plasma samples contain parent drug alone or parent drug plus inhibitory metabolites, the rank order approach described above can be applied to the results obtained with the clinical plasma samples to guide the need or prioritization of subsequent clinical DDI studies, as illustrated in FIGS. 3A-3D. For example, if CYP inhibition by the clinical plasma samples followed the rank order: CYP3A4>CYP2D6>CYP1A2>CYP2B6>CYP2C8>CYP2C9>CYP2C19, then CYP3A4 is identified as the enzyme most likely to be inhibited in vivo by a combination of both the parent drug and its circulating metabolites. The rank order approach guides the prioritization of clinical DDI studies, as shown in FIGS. 3B-3D. If, on the other hand, the clinical plasma samples cause no inhibition of any of the seven CYP enzymes listed in Table 1 (those of particular concern to the FDA and EMA) then no clinical studies of CYP inhibition would be indicated, as shown in FIG. 3A. It should be emphasized that the ex vivo testing paradigm with clinical plasma samples will establish the rank order of CYP inhibition by both the parent drug and its circulating metabolites whereas the current in vitro tests available today are focused on establishing the rank order of CYP inhibition by only the parent drug, and provide an incomplete picture of DDI potential.

Figure 4:
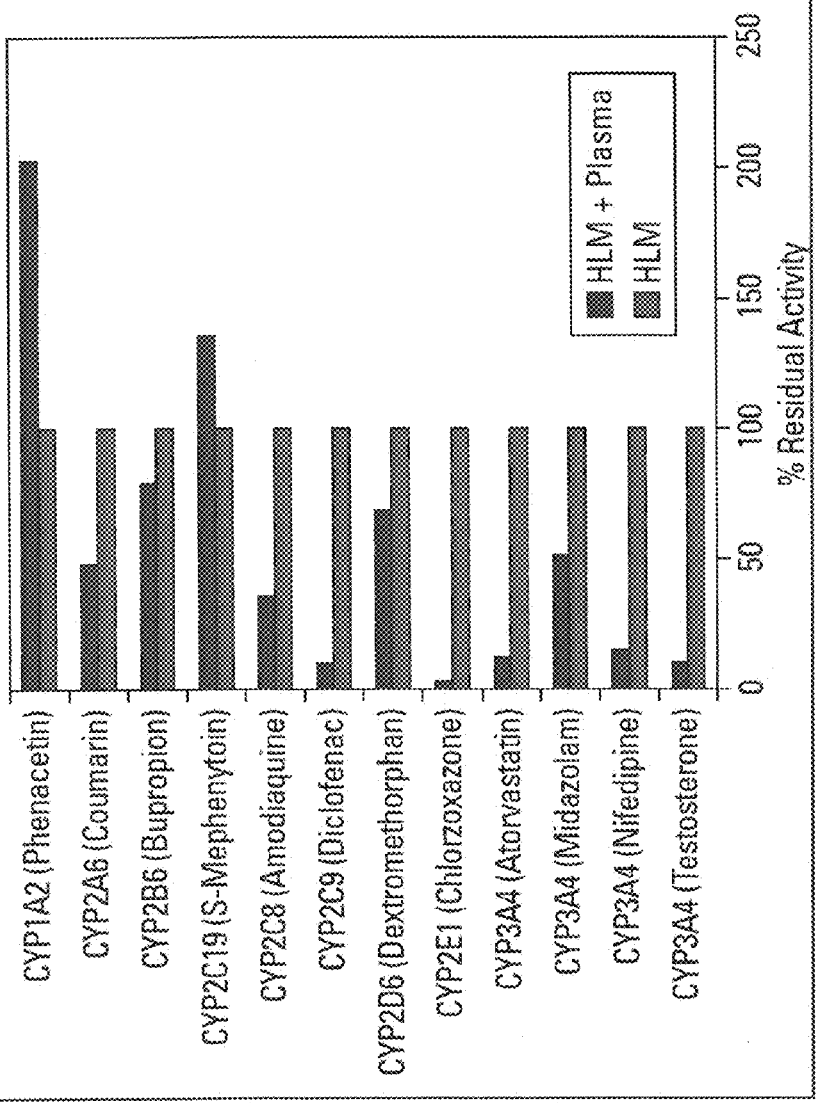
FIG. 4 (adapted from FIG. 1, Kazmi et al. 2009) shows that adding plasma to human liver microsomes causes a decrease in all CYP enzymes (albeit to different extents) due to binding of the substrates to plasma protein.
Figure 5:
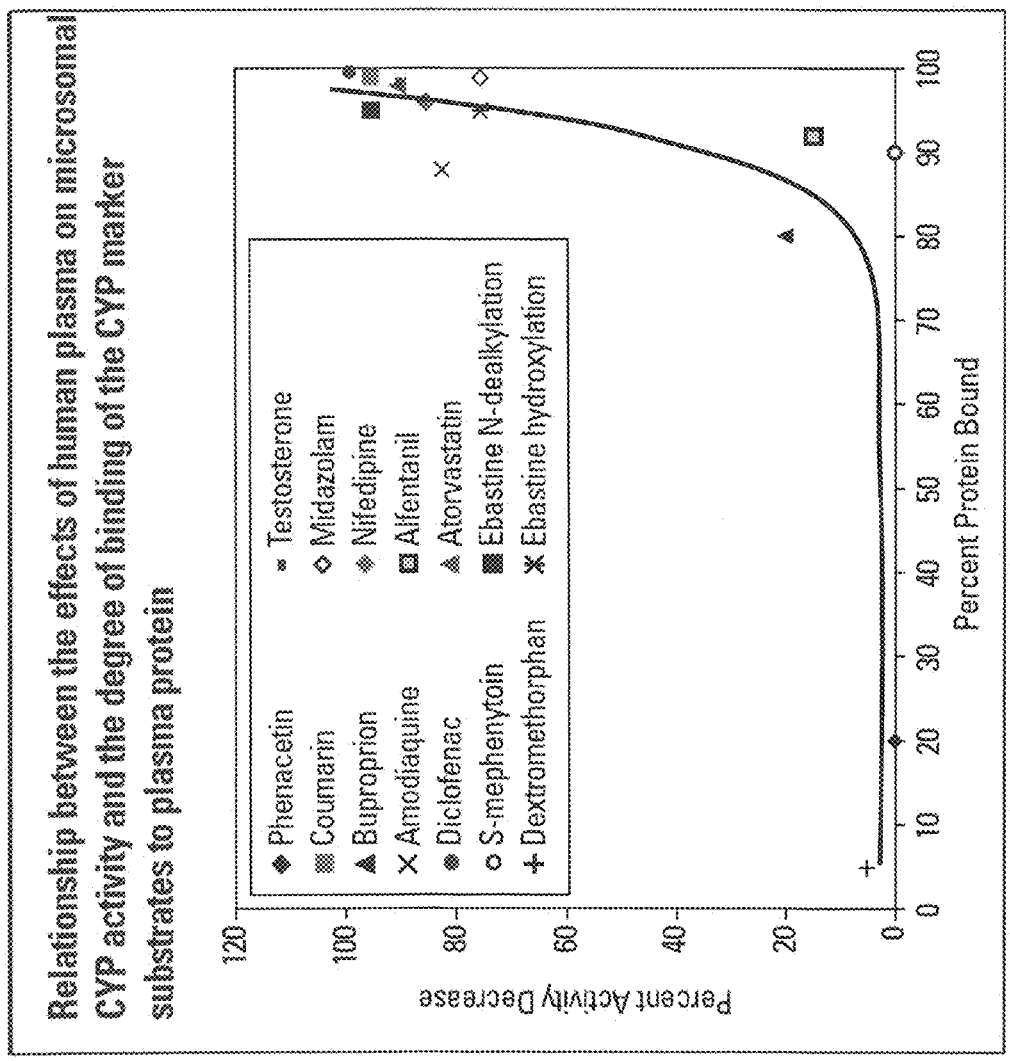
FIG. 5 (adapted from FIG. 2, Kazmi et al. 2009) shows the positive relationship between the extent of substrate binding to plasma protein and the magnitude of the decrease in CYP activity in human liver microsomes.
Figure 6:
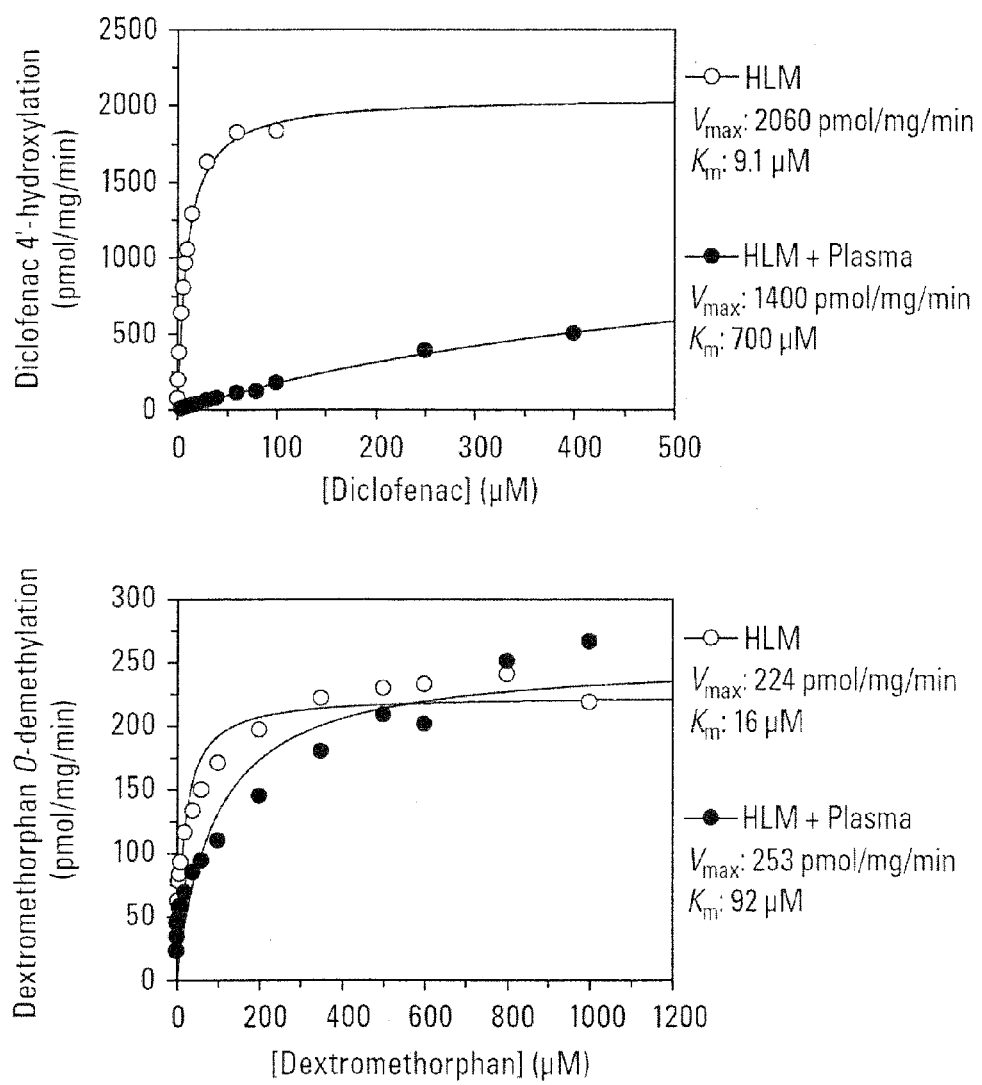
FIG. 6 (adapted from FIG. 4, Kazmi et al. 2009) shows that adding plasma to human liver microsomes causes a relatively large increase in Km (Michaelis constant) for diclofenac (a substrate for CYP2C9) but only a relatively small increase in Km for dextromethorphan (a substrate for CYP2D6)

When in vitro CYP inhibition assays are performed in simple (plasma-free) buffered solutions (as is usually the case), the final concentration of CYP marker substrate in the incubation is usually selected to be equal to its Km (Michaelis constant), which is the concentration of substrate supporting half the maximum reaction rate (Vmax). This principle is not followed when plasma is added to the incubation because some—but not all—of the marker substrates bind extensively to plasma protein, which lowers their free (unbound) concentration, which represents the concentration of substrate freely available to interact with CYP enzymes. Previous work has shown that by decreasing the free concentration of substrate, the addition of plasma to the in vitro test system slows that rate of metabolism of marker substrates by CYP enzymes, albeit to varying extents (FIG. 4; Kazmi et al. 2009). The extent to which CYP activity decreases in the presence of plasma is related to the degree of substrate binding to plasma protein, as shown in FIG. 5. In some cases, such as dextromethorphan and R-bufuralol (two substrates metabolized by CYP2D6), the addition of plasma causes a relatively modest increase in Km (less than six fold), as shown in Table 5 (for human hepatocytes) and FIG. 6 (for human liver microsomes). On the other hand, in the case of the CYP2C9 substrate diclofenac, which binds extensively to albumin in plasma (>99%), the addition of plasma to hepatocytes or human liver microsomes increases the Km for diclofenac more than 40 fold, as shown in Table 5 and FIG. 6.

TABLE 5

Effects of human plasma versus cell culture medium (HMM) on the affinity (Km) with which marker substrates bind to three CYP enzymes in human hepatocytes

| Substrate | CYP Enzyme | Km ($\mu$M) | | Increase in Km |
| --- | --- | --- | --- | --- |
| | | Medium | Plasma | |
| Diclofenac | CYP2C9 | 34.58 ± 2.14 | 1408 ± 304 | 41 fold |
| (R)-Bufuralol | CYP2D6 | 12.22 ± 1.42 | 54.83 ± 7.38 | 4.5 fold |
| Midazolam | CYP3A4 | 8.11 ± 0.65 | 45.83 ± 4.38 | 5.7 fold |

(Adapted from Table 1 in Mao et al., 2012)

Accordingly, when clinical plasma samples are added to the in vitro test system, the concentration of CYP marker substrate is not selected to equal Km, but is selected to be clinically relevant (e.g., equal to Cmax), which in most cases will be below Km in the presence of plasma. In this way, the marker substrate, the inhibitory drug and any inhibitory metabolites are all present in the test system under in vitro conditions that closely match in vivo conditions with respect to both their total concentration and free (unbound) concentrations in plasma.

The decrease in CYP activity associated with the addition of plasma to the in vitro test system is not due to inactivation or destruction of the enzymes. Previous work demonstrated that human liver microsomes incubated with plasma could be re-isolated (pelleted) by ultracentrifugation. (Kazmi et al. 2009). When resuspended in plasma-free buffer, the microsomes showed no loss of CYP activity, indicating that plasma has no irreversible effect on CYP activity but causes a decrease in the rate of reactions catalyzed by CYP enzymes due to the binding of the marker substrates to plasma protein.

Like the CYP marker substrate, the investigational drug and its metabolite(s) may also bind to plasma protein, which will lower their free (unbound) concentration. The relative effect of plasma protein binding on the free concentration of marker substrate to the free concentration of drug/metabolites determines whether plasma increases or decreases the degree of inhibition of CYP activity (measured as $IC_{50}$). For example, the addition of plasma to human hepatocytes or human liver microsomes has a modest effect on the inhibition of CYP2D6 by quinidine (the $IC_{50}$ value changed less than twofold), but it increased the inhibitory effect of voriconazole on CYP3A4 ($IC_{50}$ decreased about 7 fold), and decreased the inhibitory effect of sulfaphenazole on CYP2C9 ($IC_{50}$ increased more than 10 fold), as shown in Table 6.

TABLE 6

Effect of human plasma on the inhibition (IC$_{50}$) of various CYP enzymes in human hepatocytes

| CYP enzyme | Inhibitor | IC$_{50}$ Medium | IC$_{50}$ Plasma | Effect of plasma on IC$_{50}$ |
|---|---|---|---|---|
| CYP2C9 | Fluconazole | 53.96 ± 2.95 | 14.34 ± 1.27 | Decrease |
|  | Miconazole | 2.12 ± 0.37 | 2.02 ± 0.37 | No effect[a] |
|  | Fluvastatin | 4.07 ± 1.84 | 6.78 ± 1.01 | No effect |
|  | Sulfaphenazole | 0.29 ± 0.06 | 9.49 ± 1.89 | Increase |
|  | Ibuprofen | 151.30 ± 29.25 | >1200 | Increase |
|  | Tolbutamide | 101.08 ± 22.70 | >1200 | Increase |
| CYP2D6 | Quinidine | 0.03 ± 0.01 | 0.02 ± 0.01 | No effect |
|  | Sertraline | 3.10 ± 0.34 | 13.07 ± 3.49 | Increase |
|  | Diphenhydramine | 1.71 ± 0.19 | 30.54 ± 4.34 | Increase |
|  | Paroxetine | 0.03 ± 0.01 | 0.07 ± 0.02 | Increase |
|  | Fluoxetine | 0.04 ± 0.00 | 0.35 ± 0.09 | Increase |
|  | Duloxetine | 0.22 ± 0.04 | 0.67 ± 0.37 | Increase |
| CYP3A4 | Fluconazole | 27.00 ± 1.50 | 7.61 ± 2.67 | Decrease |
|  | Voriconazole | 22.40 ± 4.90 | 3.01 ± 0.58 | Decrease |
|  | Conivaptan | 1.90 ± 0.18 | 1.70 ± 0.56 | No effect |
|  | Ketoconazole | 0.28 ± 0.02 | 1.26 ± 0.23 | Increase |
|  | Nefazodone | 0.49 ± 0.08 | 1.70 ± 0.31 | Increase |

Figure 7:
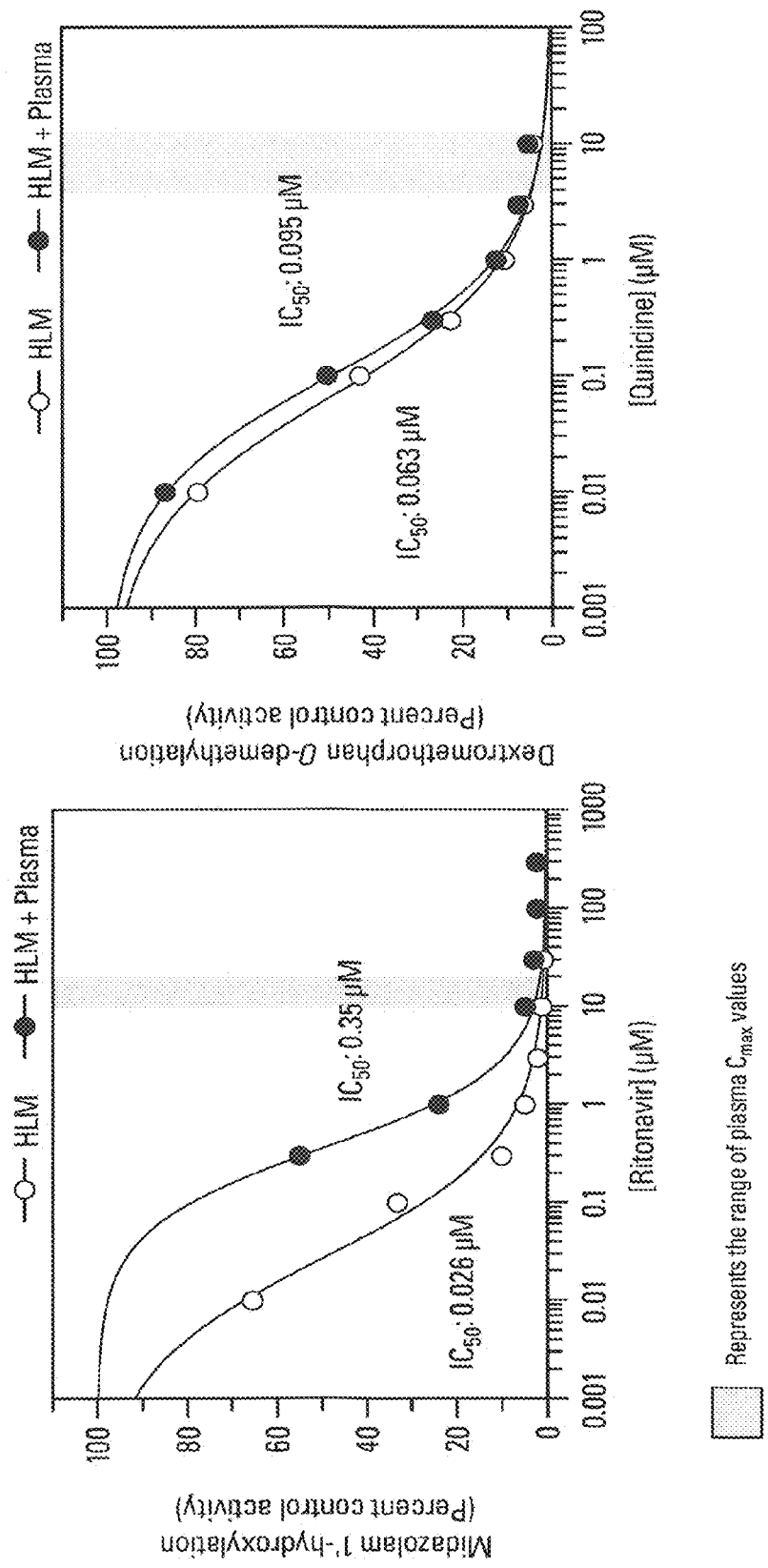
FIG. 7 (adapted from FIG. 5, Kazmi et al. 2009) shows marked inhibition of CYP2D6 by quinidine and marked inhibition of CYP3A4 by ritonavir when these drugs are added to human liver microsomes in human plasma at clinically relevant concentrations.

(Adapted from Table 2 in Mao et al., 2012)
[a] No effect means less than a two-fold difference Previous studies have favorably evaluated CYP inhibition in human hepatocytes incubated in the presence and absence of plasma (blank plasma samples, not clinical plasma samples) and concluded that the addition of plasma improved the prediction of clinical DDIs. It must be emphasized, however, that all previous studies of CYP inhibition have been performed in plasma-free incubations or incubations containing control (blank) plasma/serum. None of the studies involved adding clinical plasma samples to the test system to establish the ability of the parent drug and its metabolites to cause CYP inhibition or any other DDI effects. The present invention enables drugs and their metabolites to be identified as perpetrators of DDIs. The ability of the new invention to detect CYP inhibition by a drug (a known CYP inhibitor) present in plasma at clinically relevant concentrations is supported by FIG. 7. When added to human liver microsomes in plasma (95%, v/v) at drug concentrations equal to or less than their clinical plasma Cmax values, ritonavir inhibited CYP3A4 and quinidine inhibited CYP2D6, just as they do in vivo. (Kazmi et al; 2009). Ritonavir and quinidine are recognized by the FDA as strong inhibitors of CYP activity in vivo. It is noteworthy, therefore, that at concentrations close to plasma Cmax ritonavir and quinidine caused near complete inhibition (>90%) of CYP3A4 and CYP2D6 activity, respectively.

One of the most complex mechanisms of CYP inhibition is the inhibition of CYP2C8 by gemfibrozil, which caused, in some cases, a lethal interaction with cerivastatin (now withdrawn). Previous work determined that a metabolite of gemfibrozil, rather than gemfibrozil itself, was responsible for this clinically significant drug interaction. The inhibitory metabolite was not formed by cytochrome P450 but by another drug-metabolizing enzyme (UDP-glucuronosyltransferase) that converted gemfibrozil to gemfibrozil glucuronide. This metabolite is not only a potent inhibitor of CYP2C8 but gemfibrozil glucuronide is a metabolism-dependent inhibitor (MDI or TDI) of CYP2C8; as such it inactivates the enzyme. The mechanism of CYP2C8 inactivation by gemfibrozil is relevant to the invention for two reasons. First, gemfibrozil glucuronide is a circulating metabolite; in fact it is present in plasma at relatively high concentrations (~20 µM). Second, the presence of a MDI/TDI in plasma underscores important advantages of the invention, which can use a pre-incubation step (in which the clinical plasma samples are incubated with the test system prior to the addition of the marker substrate) to identify the presence of circulating parent drug and any metabolites that might be further converted to metabolites that inactivate CYP enzymes.

Figure 8:
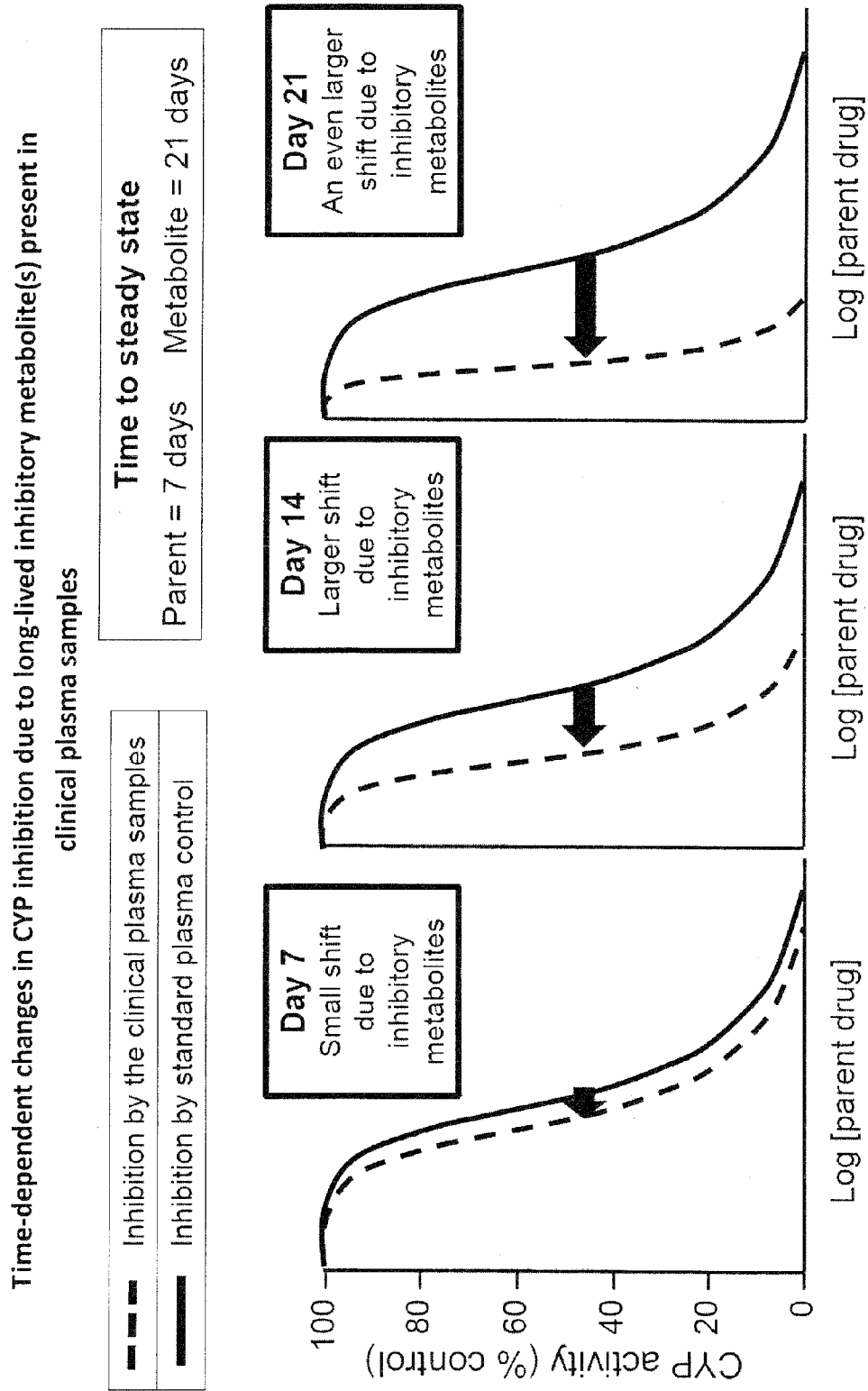
FIG. 8 shows how a drug with a long-lived inhibitory metabolite (long-lived relative to the parent drug) will cause a time-dependent increase in the magnitude of CYP inhibition by clinical plasma samples relative to blank plasma samples spiked with a matching concentration of parent drug.

Some inhibitory metabolites have a considerably longer half-life than the parent drug. For example norfluoxetine, a metabolite of fluoxetine, has a plasma half-life of about 16 days, which is considerably longer than the plasma half-life of fluoxetine (4-6 days). In such cases, the metabolite will continue to accumulate in plasma after the parent drug has reached steady state. As shown in FIG. 8, applying the invention to clinical plasma samples collected at different times during a multiple-dose study will reveal the presence of long-lived inhibitory metabolites by a time-dependent increase in the magnitude of the difference in CYP inhibition between the clinical plasma samples and the blank plasma samples spiked with matching concentrations of the parent drug.

Importantly, the invention can identify the presence of circulating metabolites with DDI perpetrator potential even without knowing the identity of the metabolites. Accordingly, the invention will have particular utility when circulating drug metabolites cannot be identified or synthesized to permit traditional in vitro testing.

Although the invention is described in terms of using clinical plasma samples from human subjects administered a drug, it could also be used to evaluate the presence of metabolites with DDI potential in plasma samples from other drug-treated species (e.g., non-human mammals, such as rodents (rats, mice, rabbits), dogs, cats, pigs, horses, and monkeys), as well as plasma/serum from so-called humanized animal models (genetically modified non-human mammals, harboring human hepatocytes). Although the invention is described primarily with respect to small molecule drugs, it could also be used to evaluate the presence of metabolites with DDI potential in plasma samples from humans or nonclinical species treated or exposed to other foreign or exogenous chemicals such as dietary/nutritional supplements, herbal remedies, illicit drugs, industrial chemicals, and other xenobiotics. The invention is also applicable to drugs (both approved and investigational) regardless of their route of administration.

The invention could also be used to measure cellular toxicity, mutagenicity, and/or other end-points.

ABBREVIATIONS AND TERMS

Unless otherwise noted, technical terms are used according to conventional usage.

ADME Absorption, distribution, metabolism and elimination (four major phases of drug disposition).

Administer or Administration To provide or give a subject an agent, such as an investigational drug or therapeutic, by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

AUC Integrated area under the plasma concentration versus time curve after a single dose of drug or at steady state.

CITCO 6-(4-Chlorophenyl)imidazo[2,1-b][1,3]thiazole-5-carbaldehyde-O-(3,4-dichlorobenzyl)oxime Clearance The volume of blood cleared of drug per unit time.

Cmax Peak plasma concentration of drug after its administration.

CYP Cytochrome P450 (a major class of drug-metabolizing enzymes).

DDI Drug-drug interaction.

DME Drug-metabolizing enzyme.

$EC_{50}$ The concentration of drug causing 50% induction of a drug-metabolizing enzyme.

EMA European Medicines Administration (a regulatory agency in Europe).

Emax The maximum level of induction of a drug-metabolizing enzyme.

Ex vivo An experiment or study that combines an in vivo component with an in vitro component, for example, experimentation or measurements done in or on living tissue in an artificial environment outside the organism with the minimum alteration of the natural conditions.

FDA Food and Drug Administration (a regulatory agency in the United States).

Half-life The time required for the concentration of a drug to reach half its original value.

Hepatocytes Liver cells. Hepatocytes have the ability to metabolize, detoxify, and inactivate exogenous compounds such as drugs.

Isolated hepatocytes Hepatocytes that have been obtained from a particular source, such as an organ donor, and specifically those that are substantially separated or purified away from other cell types, or purified away from other types of tissue, such as adipose tissue or fibrotic tissue.

HLM Human liver microsomes.

$IC_{50}$ The concentration of drug causing 50% inhibition of a drug-metabolizing enzyme.

Induction A drug-mediated increase in the levels of a drug-metabolizing enzyme, which can increase the rate of drug metabolism (which is an important cause of DDI).

Inhibition A drug-mediated decrease in the activity of a drug-metabolizing enzyme, which can decrease the rate of drug metabolism (which is an important cause of DDI).

In vitro An experiment or study performed outside of a living organism (literally "in glass," such as test tubes).

In vivo An experiment or study performed in a living organism (such as a human subject or laboratory animal in the case of clinical and nonclinical studies).

Ki Inhibition constant: a measure of the affinity or potency with which a drug inhibits a drug-metabolizing enzyme.

Km Michaelis constant: a measure of the affinity with which a drug (substrate) binds to the enzyme involved in its metabolism.

MDI Metabolism-dependent inhibition (also known as time-dependent inhibition).

Metabolite The product of a drug formed by chemical modification (e.g., in vivo modification within the body), such as the loss of a methyl group in the conversion of fluoxetine (drug) to norfluoxetine (metabolite).

Pharmacokinetics The study of the time course of changes in the concentration of a drug and/or its metabolites.

Steady state When the pharmacokinetics of a drug are the same between one dose and the next.

TDI Time-dependent inhibition (also known as metabolism-dependent inhibition).

Transporter A membrane-bound protein that facilitates the movement of a drug and/or its metabolites from one side of a biological membrane to the other. Transporters can function to facilitate drug/metabolite uptake into a cell or drug/metabolite efflux out of a cell.

Vmax The maximum rate of an enzyme-catalyzed reaction.

REFERENCES

EMA (2012). European Medicines Agency: Guideline on the investigation of drug interactions. www.ema.europa.eu/ema/pages/includes/document/open_document.jsp?webContentId=WC500129606

EMA (2006). European Medicines Agency: Guideline on the investigation of drug interactions. www.ema.europa.eu/ema/pages/includes/document/open_document.jsp?webContentId=WC500090112

FDA (2012). US Food and Drug Administration: Guidance for Industry. Drug interaction studies—Study design, data analysis, implications for dosing, and labeling recommendations. www.fda.gov/downloads/Drugs/GuidanceComplianceRegulatoryInformation/Guidances/UCM292362.pdf)

FDA (2006). US Food and Drug Administration: Guidance for Industry: Drug Interaction Studies—Study Design, Data Analysis, and Implications for Dosing and Labeling. Draft Guidance. www.fda.gov/cder/drug/drugInteractions/default.htm Grimm S W, Einolf H J, Hall S D, He K, Lim H-K, Ling K-H J, Lu C, Nomeir A A, Seibert E, Skordos K W, Tonn G R, Van Horn R, Wang R W, Wong Y N, Yang T J and Obach R S. The conduct of in vitro studies to address time-dependent inhibition of drug-metabolizing enzymes: A perspective of the Pharmaceutical Research and Manufacturers of America. *Drug Metab Dispos* 37:1355-1370 (2009).

Kazmi F, Buckley D B, Yerino P, Ogilvie B W and Parkinson A. Effects of plasma on cytochrome P450 (CYP) inhibition studies in human liver microsomes (HLM): Consequences on in vitro to in vivo extrapolations (IVIVE). Poster 192 at the annual meeting of the International Society for the Study of Xenobiotics (ISSX) in Baltimore, Md., USA (2009).

Mao J, Mohutsky M A, Harrelson J P, Wrighton S A and Hall S D. Prediction of CYP3A-mediated drug-drug interactions using human hepatocytes suspended in human plasma. *Drug Metab Dispos*, 39: 591-602 (2011).

Mao J, Mohutsky M A, Harrelson J P, Wrighton S A and Hall S D. Predictions of cytochrome P450-mediated drug-drug Interactions using cryopreserved human hepatocytes: Comparison of plasma and protein-free media incubation conditions. *Drug Metab Dispos*, 40: 706-716 (2012).

Yeung C K, Fujioka Y, Hachad, Levy R H and Isoherranen N. Are circulating metabolites important in drug-drug interactions?: Quantitative analysis of risk prediction and inhibitory potential. *Clin Pharmacol Ther* 89: 105-113 (2011).

What is claimed:

1. A method of analyzing circulating drug metabolites with drug interaction potential, said method comprising:
   providing a clinical plasma sample from a subject, wherein said clinical plasma sample comprises a drug at a first concentration and a plurality of metabolites of said drug;
   providing a standard control plasma sample comprising said drug at a standard concentration, said standard control plasma sample being essentially free of metabolites of said drug, wherein said standard concentration is substantially the same as, or brackets said first concentration;
   adding said clinical plasma sample to a first in vitro test system;
   adding said standard control plasma sample to a second in vitro test system;
   assaying said clinical plasma sample and said standard control plasma sample for activity or expression of drug-metabolizing enzymes and/or drug transporters in said first and second in vitro test systems; and
   analyzing changes in activity or expression of drug-metabolizing enzymes and/or drug transporters in said first and second in vitro test systems to determine circulating drug metabolites with drug interaction potential based upon inhibitory and/or inducing effects on said drug-metabolizing enzymes and/or drug transporters.

2. The method of claim 1, wherein said first and second in vitro test systems comprise hepatocytes, liver or intestinal microsomes, subcellular fractions or vesicles, recombinant or purified drug-metabolizing enzymes and/or drug transporters, and/or isolated cells expressing one or more drug-metabolizing enzymes and/or drug transporters, and/or cell lines expressing one or more drug-metabolizing enzymes and/or drug transporters.

3. The method of claim 2, wherein said first and second in vitro test systems further comprise enzyme and/or transporter marker substrates and/or ligands.

4. The method of claim 1, wherein said analyzing comprises:
   detecting changes in activity or expression of drug-metabolizing enzymes and/or drug transporters in said first and second in vitro test systems, wherein said changes indicate inhibitory and/or inducing effects on said drug metabolizing enzymes and/or drug transporters; and
   comparing the inhibitory and/or inducing effects of the clinical plasma sample on said drug-metabolizing enzymes and/or drug transporters in said first in vitro test system to the inhibitory and/or inducing effects of the standard control plasma sample on said drug-metabolizing enzymes and/or drug transporters in said second in vitro test system.

5. The method of claim 4, wherein said first in vitro test system yields a first set of results and wherein said second in vitro test system yields a second set of results.

6. The method of claim 5, wherein when said first set of results is substantially identical to said second set of results, the inhibitory and/or inducing effects are attributed to said drug.

7. The method of claim 5, wherein when the inhibitory and/or inducing effects in said first set of results is substantially greater than the inhibitory and/or inducing effects in said second set of results, the inhibitory and/or inducing effects are attributed primarily to said drug metabolites.

8. The method of claim 7, wherein when no inhibitory and/or inducing effects are present in said second set of results, the inhibitory and/or inducing effects are attributed solely to said drug metabolites.

9. The method of claim 1, further comprising a rank order determination of the inhibitory and/or inducing metabolites on two or more drug-metabolizing enzymes or transporters.

10. The method of claim 1, wherein said providing a clinical plasma sample comprises:
    administering a drug to a subject;
    collecting a biological sample from said subject, wherein said biological sample comprises plasma or serum.

11. The method of claim 10, wherein said biological sample is whole blood, further comprising separating said plasma or serum from said blood.

12. The method of claim 10, wherein said control plasma sample comprises plasma collected from said subject prior to administering said drug to said subject.

13. The method of claim 1, wherein said providing a standard control plasma sample comprises:
    measuring the concentration of said drug in said clinical plasma sample; providing a blank plasma; and
    adding said drug to said blank plasma in vitro in an amount that is substantially the same as, or brackets said concentration of said drug in said clinical plasma sample.

14. The method of claim 13, wherein said blank plasma is essentially free of said drug prior to adding said drug to said blank plasma.

15. The method of claim 1, further comprising:
    providing a positive control plasma sample and a negative control plasma sample, said positive control plasma sample comprising inducers and/or inhibitors of drug metabolizing enzymes or drug transporters, said negative control plasma sample being essentially free of said drug or its metabolites;
    adding said positive control plasma sample to a third in vitro test system; adding said negative control plasma sample to a fourth in vitro test system; and analyzing the changes in activity or expression of drug-metabolizing enzymes and/or drug transporters in said third and fourth in vitro test systems to establish positive and negative control values.

16. The method of claim 15, comparing said positive and negative control values to said changes in activity or expression of drug-metabolizing enzymes and/or drug transporters in said first and second in vitro test systems.

* * * * *